(12) United States Patent
Kugler et al.

(10) Patent No.: US 10,205,108 B2
(45) Date of Patent: Feb. 12, 2019

(54) COMPOUND

(71) Applicant: CAMBRIDGE DISPLAY TECHNOLOGY LIMITED, Cambridgeshire (GB)

(72) Inventors: Thomas Kugler, Cambridge (GB); Tania Zuberi, Harrow (GB); Richard Wilson, Cambridge (GB); Jeremy Burroughes, Cambridgeshire (GB)

(73) Assignee: CAMBRIDGE DISPLAY TECHNOLOGY LIMITED, Cambridgeshire (GB)

( * ) Notice: Subject to any disclaimer, the term of this patent is extended or adjusted under 35 U.S.C. 154(b) by 0 days.

(21) Appl. No.: 15/331,335

(22) Filed: Oct. 21, 2016

(65) Prior Publication Data
US 2017/0040556 A1 Feb. 9, 2017

Related U.S. Application Data

(62) Division of application No. 14/026,962, filed on Sep. 13, 2013, now abandoned.

(30) Foreign Application Priority Data

Sep. 13, 2012 (GB) .................................. 1216309.3

(51) Int. Cl.
| | |
|---|---|
| H01L 51/00 | (2006.01) |
| C07F 7/08 | (2006.01) |
| C09K 11/06 | (2006.01) |
| H05B 33/14 | (2006.01) |
| C09K 11/02 | (2006.01) |
| H01L 51/50 | (2006.01) |

(52) U.S. Cl.
CPC .......... *H01L 51/0094* (2013.01); *C07F 7/081* (2013.01); *C09K 11/025* (2013.01); *C09K 11/06* (2013.01); *H01L 51/0035* (2013.01); *H01L 51/0039* (2013.01); *H01L 51/0059* (2013.01); *H01L 51/0062* (2013.01); *H01L 51/0067* (2013.01); *H01L 51/0085* (2013.01); *H05B 33/14* (2013.01); *C09K 2211/1007* (2013.01); *C09K 2211/1014* (2013.01); *C09K 2211/1029* (2013.01); *C09K 2211/185* (2013.01); *H01L 51/0036* (2013.01); *H01L 51/5016* (2013.01); *H01L 51/5072* (2013.01); *H01L 51/5076* (2013.01); *H01L 51/5088* (2013.01); *H01L 2251/308* (2013.01)

(58) Field of Classification Search
CPC ................................ C09K 11/06; C07F 7/0818
See application file for complete search history.

(56) References Cited

U.S. PATENT DOCUMENTS

| | | | |
|---|---|---|---|
| 4,539,570 | A | 9/1985 | Moore |
| 5,723,873 | A | 3/1998 | Yang |

(Continued)

FOREIGN PATENT DOCUMENTS

| | | |
|---|---|---|
| EP | 0 901 176 A2 | 3/1999 |
| EP | 0 947 123 A1 | 10/1999 |

(Continued)

OTHER PUBLICATIONS

Kwon et al. (Material Research Society Symposium Proceedings, vol. 1197 (2010) 1197-D03-05.*

(Continued)

*Primary Examiner* — Kuo Liang Peng
(74) *Attorney, Agent, or Firm* — Marshall, Gerstein & Borun LLP

(57) ABSTRACT

The present invention relates to a compound of general formula (I) which can transport holes in an organic optoelectronic device, and to blends and solutions comprising the compound of general formula (I):

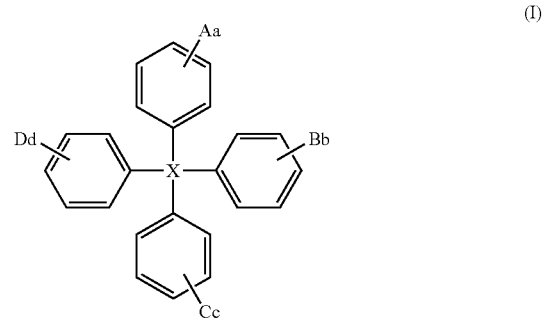

wherein
X is C, Si or Ge;
A is a group of formula (II)

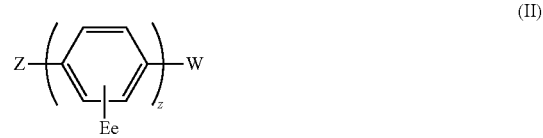

wherein Z is N, P, NH, O or S;
E is $C_{1-10}$ alkyl or H;
W is substituted or unsubstituted $C_{5-14}$ aryl or substituted or unsubstituted $C_{6-16}$ alkyl;
e is an integer from 1 to 4; and
z is 1 or 2;

(Continued)

B, C and D are each independently A, H, $C_1$-$C_{12}$ alkyl, $C_{5-14}$ aryl or OH; and a, b, c and d are each independently an integer from 1 to 5.

19 Claims, 11 Drawing Sheets

(56) References Cited

U.S. PATENT DOCUMENTS

| | | | |
|---|---|---|---|
| 5,798,170 | A | 8/1998 | Zhang et al. |
| 6,677,090 | B1 | 1/2004 | Tong et al. |
| 7,238,435 | B2 | 7/2007 | Kamatani et al. |
| 2010/0033086 | A1 | 2/2010 | Mikami et al. |
| 2011/0006294 | A1 | 1/2011 | Tanaka et al. |
| 2011/0124808 | A1 | 5/2011 | Akino et al. |
| 2011/0127517 | A1 | 6/2011 | Nakatani |
| 2011/0272686 | A1 | 11/2011 | Ohuchi et al. |

FOREIGN PATENT DOCUMENTS

| | | |
|---|---|---|
| EP | 1 245 659 | 10/2002 |
| EP | 1 424 350 A1 | 6/2004 |
| EP | 2 123 691 A1 | 11/2009 |
| GB | 2 435 194 A | 8/2007 |
| WO | WO-90/13148 A1 | 11/1990 |
| WO | WO-95/06400 A1 | 3/1995 |
| WO | WO-98/10621 A1 | 3/1998 |
| WO | WO-98/57381 A1 | 12/1998 |
| WO | WO-99/48160 A1 | 9/1999 |
| WO | WO-00/48258 A1 | 8/2000 |
| WO | WO-00/53656 A1 | 9/2000 |
| WO | WO-00/70655 A2 | 11/2000 |
| WO | WO-01/19142 A1 | 3/2001 |
| WO | WO-01/81649 A1 | 11/2001 |
| WO | WO-02/31896 A2 | 4/2002 |
| WO | WO-2002/066552 A1 | 8/2002 |
| WO | WO-02/84759 A1 | 10/2002 |
| WO | WO-2002/083760 A2 | 10/2002 |
| WO | WO-2002/092723 A1 | 11/2002 |
| WO | WO-03/18653 A1 | 3/2003 |
| WO | WO-03/22908 A1 | 3/2003 |
| WO | WO-2005/052027 A1 | 6/2005 |
| WO | WO-2008/016090 A1 | 2/2008 |
| WO | WO-2008/111658 A1 | 9/2008 |
| WO | WO-2009/110642 A1 | 9/2009 |
| WO | WO-2009/157424 A1 | 12/2009 |
| WO | WO-2010/013724 A1 | 2/2010 |
| WO | WO-2010/049546 A1 | 5/2010 |
| WO | WO-2010/084977 A1 | 7/2010 |

OTHER PUBLICATIONS

Chin et al. (Journal of Physics D: Applied Physics, 41(21) (2008) 1-6).*

Li et al., Organic Light Emitting Materials and Devices, CRC Press (2007). Table of Contents only.

Michaelson, "The work function of the elements and its periodicity", *J. Applied Physics*, 48(11): 4729-4733 (1977).

Niu et al., "Thermal Annealing Below the Glass Transition Temperature: A General Way to Increase Performance of Light-Emitting Diodes Based on Copolyfluorenes," *Appl. Phys. Lett.*, 81(4):634-636 (2002).

Tokito et al., "Metal oxides as a hole-injecting layer for an organic electroluminescent device", *J. Phys. D: Appl. Phys.*, 29:2750-2753 (1996).

Yamaguchi et al., "Effects of B and C on the Ordering of $L1_0$-CoPt Thin Films," *Appl. Phys. Lett.*, 79(5):2001-2003 (2001).

* cited by examiner

COMPOUND

CROSS-REFERENCE TO RELATED APPLICATION

This application is a divisional of U.S. patent application Ser. No. 14/026,962, filed Sep. 13, 2013, which claims priority to Great Britain Application No. 1216309.3, filed Sep. 13, 2012, all of which are expressly incorporated herein by reference and made a part hereof.

FIELD OF THE INVENTION

The present invention relates to a compound which can transport holes in an organic optoelectronic device and to blends and solutions comprising the compound. The invention is also concerned with organic optoelectronic devices comprising an active layer which comprises the compound or blend and to methods for making the devices.

BACKGROUND

Organic electronic devices provide many potential advantages including inexpensive, low temperature, large scale fabrication on a variety of substrates including glass and plastic. Organic light emitting diode displays provide additional advantages as compared with other display technologies—in particular they are bright, colourful, fast-switching and provide a wide viewing angle. OLED devices (which here includes organometallic devices and devices including one or more phosphors) may be fabricated using either polymers or small molecules in a range of colours and in multicoloured displays depending upon the materials used. For general background information reference may be made, for example, to WO90/13148, WO95/06400, WO99/48160 and U.S. Pat. No. 4,539,570, as well as to "Organic Light Emitting Materials and Devices" edited by Zhigang Li and Hong Meng, CRC Press (2007), ISBN 10: 1-57444-574X, which describes a number of materials and devices, both small molecule and polymer.

In its most basic form an organic light emitting diode (OLED) comprises a light emitting layer which is positioned in between an anode and a cathode. Frequently a hole injection layer is incorporated in between the anode and the light emitting layer. It functions to decrease the energy difference between the work function of the anode and the highest occupied molecular orbital (HOMO) of the light emitting layer thereby increasing the number of holes introduced into the light emitting layer. In operation holes are injected through the anode, and if present the hole injection layer, into the light emitting layer and electrons are injected into the light emitting layer through the cathode. The holes and electrons combine in the light emitting layer to form an exciton which then undergoes radiative decay to provide light.

In many OLEDs the light emitting layer comprises a light emitting compound and a charge transporting material, e.g. a electron transporting polymer. A wide range of light emitting compounds are employed. These are generally metal complexes of lanthanide or d-block metals such as iridium. Typically 40-50% wt of the light emitting layer is light emitting compound and the remainder is charge transporting material. Such devices have excellent optoelectronic properties, namely high luminance, current density and EQE for a given drive voltage as well as luminance over extended periods of time (i.e. extended device lifetime).

The drawback of such devices, however, is that the light emitting compounds, present in amounts of up to 50% wt of the light emitting layer, are expensive and this significantly increases the overall cost of the manufacture of the devices. A need therefore exists for new devices that provide comparable optoelectronic properties to todays commercially available devices but which are less expensive to prepare.

SUMMARY OF INVENTION

Thus viewed from a first aspect the present provides a compound of general formula (I):

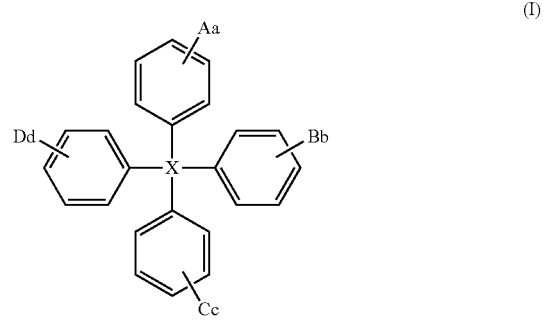

wherein
X is C, Si or Ge;
A is a group of formula (II)

wherein Z is N, P, NH, O or S;
E is $C_{1-10}$ alkyl or H;
W is substituted or unsubstituted $C_{5-14}$ aryl or unsubstituted or substituted $C_{6-16}$ alkyl;
e is an integer from 1 to 4; and
z is 1 or 2;
B, C and D are each independently A, H, $C_1$-$C_{12}$ alkyl, $C_{5-14}$ aryl or OH; and
a, b, c and d are each independently an integer from 1 to 5.

Viewed from a further aspect the present invention provides a method for making a compound as hereinbefore defined comprising reacting a compound of formula (a):

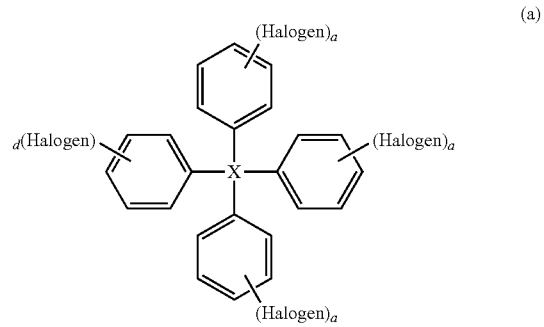

with a compound of formula (b)

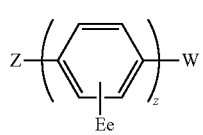

wherein X, Z, E, W, a, b, c, d, e and z are as hereinbefore defined.

Viewed from a still further aspect the present invention provides a blend comprising a compound as hereinbefore defined.

Viewed from a still further aspect the present invention provides a solution comprising a solvent and a compound or a blend as hereinbefore defined.

Viewed from another aspect the present invention provides an organic optoelectronic device comprising an anode, a cathode and an active organic layer in between said anode and cathode, wherein said active layer comprises a compound or a blend as hereinbefore defined.

Preferably the device is an organic light emitting device and the active organic layer is an organic light-emitting layer.

Viewed from yet another aspect the present invention provides a method for preparing an active layer of an organic optoelectronic device as hereinbefore defined comprising:

(i) depositing (preferably by spin coating) said active layer from a solution as hereinbefore defined; and (ii) drying said deposited layer to evaporate said solvent.

Definitions

As used herein the term "alkyl" refers to saturated, straight chained, branched or cyclic groups. Alkyl groups may be substituted or unsubstituted.

As used herein the term "haloalkyl" refers to saturated, straight chained, branched or cyclic groups in which one or more hydrogen atoms are replaced by a halo atom, e.g. F or Cl, especially F.

As used herein, the term "cycloalkyl" refers to a saturated or partially saturated mono- or bicyclic alkyl ring system containing 3 to 10 carbon atoms. Cycloalkyl groups may be substituted or unsubstituted.

As used herein, the term "heterocycloalkyl" refers to a cycloalkyl group in which one or more ring carbon atoms are replaced by at least one hetero atom such as —O—, —N— or —S—. Heterocycloalkyl groups may be substituted or unsubstituted.

As used herein the term "aromatic ring" refers to a planar ring that has 4n+2 pi electrons, wherein n is a non-negative integer.

As used herein, the term "aryl" refers to a group comprising at least one aromatic ring. The term aryl encompasses heteroaryl as well as fused ring systems wherein one or more aromatic ring is fused to a cycloalkyl ring. Aryl groups may be substituted or unsubstituted.

As used herein, the term "heteroaryl" refers to a group comprising at least one aromatic ring in which one or more ring carbon atoms are replaced by at least one hetero atom such as —O—, —N— or —S—.

As used herein the term "halogen" encompasses atoms selected from the group consisting of F, Cl, Br and I.

As used herein the term "alkenyl" refers to straight chained, branched or cyclic group comprising a double bond. Alkenyl groups may be substituted or unsubstituted.

As used herein the term "alkynyl" refers to straight chained, branched or cyclic groups comprising a triple bond. Alkynyl groups may be substituted or unsubstituted.

As used herein the term "alkoxy" refers to O-alkyl groups, wherein alkyl is as defined above.

As used herein, the term "arylalkyl" refers to an alkyl group as hereinbefore defined that is substituted with an aryl group as hereinbefore defined.

As used herein the term "blend" refers to a mixture of at least two compounds and/or polymers. Generally a blend will be a solid, e.g. powder.

As used herein the term "solution" refers to a homogeneous mixture of a compound or blend in a solvent.

As used herein the term green emitter refers to a compound that emits radiation having a wavelength in the range 490 to 560 nm.

As used herein the term red emitter refers to a compound that emits radiation having a wavelength in the range 635 to 700 nm.

As used herein the term ligating site is the part of a ligand through which the ligand is joined, e.g. bonded, to the metal centre M. A ligating site may comprise one atom or may comprise, e.g. a pi system.

DESCRIPTION OF INVENTION

The compounds of the present invention are preferably incorporated into the light emitting layer of an organic optoelectronic device. The presence of the compounds of the invention in the light emitting layer advantageously enables the amount of light emitting compound present in the layer to be decreased without compromising the optoelectronic properties of the device.

The compound of the present invention is of general formula (I):

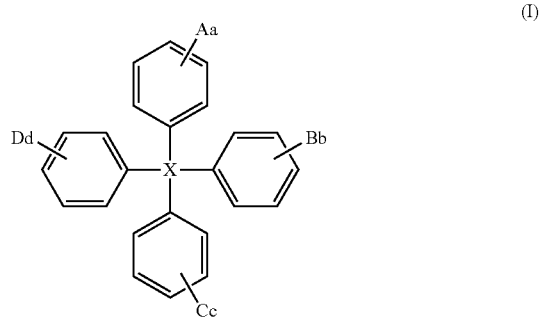

wherein
X is C, Si or Ge, preferably Si or C, especially Si;
A is a group of formula (II)

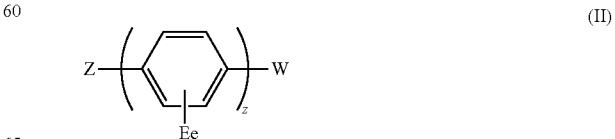

wherein Z is N, P, NH, O or S;

E is $C_{1-10}$ alkyl or H;

W is substituted or unsubstituted $C_{5-14}$ aryl or unsubstituted or substituted $C_{6-16}$ alkyl;

e is an integer from 1 to 4; and z is 1 or 2;

B, C and D are each independently A, H, $C_1$-$C_{12}$ alkyl, $C_{5-14}$ aryl or OH; and a, b, c and d are each independently an integer from 1 to 5

In many cases the compounds of the present invention may be referred to as dendrimers.

In preferred compounds of formula (I), a is 1, 2 or 3, still more preferably 1 or 2 and yet more preferably 1. When a is 2, the groups of formula A are preferably present at positions 3 and 5. When a is 1, the group of formula A is preferably present at position 4, i.e. para position. In particularly preferred compounds a is 1 and A is in the 4 or para position.

In preferred compounds of formula (I), b is 1, 2 or 3, still more preferably 1 or 2 and yet more preferably 1. When b is 2, the groups of formula B are preferably present at positions 3 and 5. When b is 1, the group of formula B is preferably present at position 4, i.e. para position. In particularly preferred compounds b is 1 and B is in the 4 or para position.

In preferred compounds of formula (I), c is 1, 2 or 3, still more preferably 1 or 2 and yet more preferably 1. When c is 2, the groups of formula C are preferably present at positions 3 and 5. When c is 1, the group of formula C is preferably present at position 4, i.e. para position. In particularly preferred compounds c is 1 and C is in the 4 or para position.

In preferred compounds of formula (I), d is 1, 2 or 3, still more preferably 1 or 2 and yet more preferably 1. When d is 2, the groups of formula D are preferably present at positions 3 and 5. When d is 1, the group of formula D is preferably present at position 4, i.e. para position. In particularly preferred compounds d is 1 and D is in the 4 or para position.

More preferred compounds of formula (I) are those of formula (Ia):

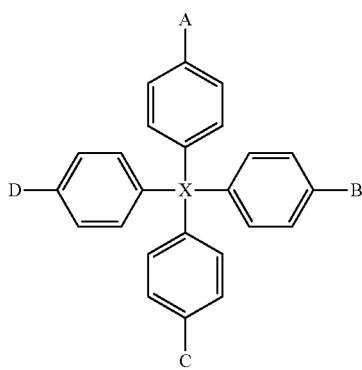

(Ia)

wherein X, A, B, C and D are as hereinbefore defined.

In preferred compounds of formula (I) B, C and D are each independently A, H, $C_1$-$C_{16}$ alkyl or $C_{5-14}$ aryl and more preferably A, H or $C_1$-$C_{16}$ alkyl. When B, C or D is alkyl it is preferably $C_{4-12}$ alkyl and more preferably $C_{6-12}$ alkyl.

In further preferred compounds of formula (I) at least one of B, C and D is a group A of formula (II). In some preferred compounds B is a group A of formula (II). In other preferred compounds C is a group A of formula (II). In still other preferred compounds D is a group A of formula (II). In particularly preferred compounds at least two of B, C and D is a group A of formula (II). B and C, B and D or C and D may, for example, be a group A of formula (II). Still more preferably each of B, C and D is a group A of formula (II).

When any or all of B, C and D is a group A, it may or may not be the same group of formula (II) as A. Preferably, however, each of A, B, C and D are the same group of formula (II).

In further preferred compounds of formula (I) E is H and e is 4. Preferably therefore the phenyl ring is solely substituted by groups Z and W. If E is not H, it is preferably $C_{1-6}$ alkyl and more preferably $C_{1-4}$ alkyl. When E is not H, e is preferably 1 or 2, more preferably 1.

In further preferred compounds of formula (I) Z is N or P and z is 2. Particularly preferably Z is N and z is 2.

Still more preferred compounds of formula (I) are those of formula (Ib):

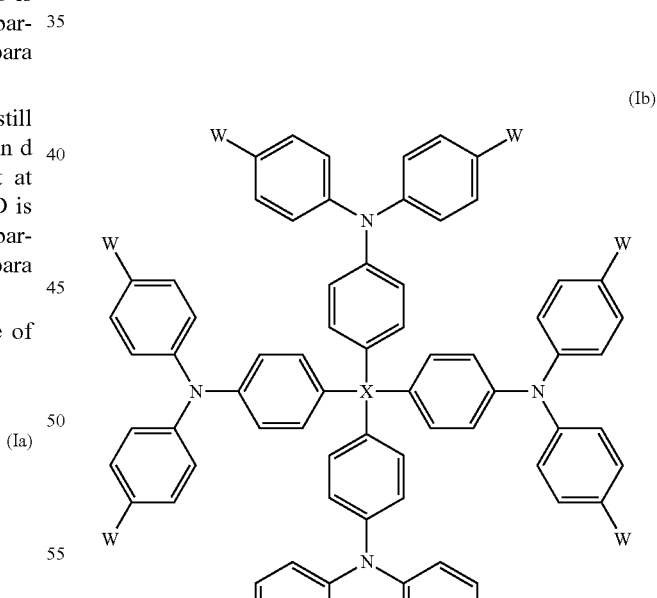

(Ib)

wherein X and W are as hereinbefore defined.

In some preferred compounds of formula (I) W is an unsubstituted or substituted $C_{6-16}$ alkyl, preferably an unsubstituted $C_{6-16}$ alkyl group. Preferred alkyl groups are $C_{6-12}$ and still more preferably $C_{6-8}$. In such compounds W is preferably hexyl or 2-ethylhexyl.

In preferred compounds of formula (I) W is an aryl group. The aryl group may comprise 4 to 14 carbon atoms, more preferably 5 to 13 carbon atoms and still more preferably 6 to 10 carbon atoms. Aryl groups optionally comprise 0, 1, 2 or 3 heteroatoms.

The aryl group may comprise one aromatic ring or may comprise one aromatic ring fused to one or more (e.g. two or three) cycloalkyl, heterocycloalkyl and/or aromatic rings. When a cycloalkyl ring is present within an aryl group it is preferably a $C_5$ or $C_6$ ring. When a heterocycloalkyl group is present in an aryl group, it is preferably a $C_5$ or $C_6$ ring and especially a $C_5$ or $C_6$ ring comprising one heteroatom.

Preferred aryl groups consist of aromatic rings. Still further preferred aryl groups are non-heteroaromatic.

In preferred compounds of formula (I) the aryl group is selected from phenyl, naphthyl, anthracenyl, phenanthrenyl, acenaphthylenyl, azulenyl, indanyl, indenyl, tetrahydronaphthalenyl, pyrrolyl, furanyl, thienyl, pyrazolyl, imidazolyl, thiazolyl, isothiazolyl, isoxazolyl, oxazolyl, oxadiazolyl, thiodiazolyl, triazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, isobenzothiophenyl, benzoxazolyl, benzisoxazolyl, cinnolinyl, phthalazinyl, pteridine, naphthyridinyl, quinoxalinyl, phthalamide, phenanthrolinyl, phthalic anhydride, indolinyl, isoindolinyl, tetrahydroisoquinolinyl, chromanyl, xanthenyl, thianthrenyl, phenoxathiinyl, phenothiazinyl, tetrahydroquinolyl, acridinyl, phenazinyl, phenothiazinyl, phenoxazinyl, fluorenyl and carbazolyl. More preferably the aryl group is selected from phenyl, naphthyl, fluorenyl and carbazolyl. Particularly preferably the aryl group is phenyl.

When W is an aryl group, it may be a substituted or unsubstituted aryl group. Preferably W is a substituted aryl group. The aryl group may be substituted at one, two, three, four or five ring atoms. Preferably, however, the aryl group is substituted at one or two ring atoms, still more preferably one ring atom. When the aryl group is phenyl and is substituted at two ring atoms, the substituents are preferably present at the 3 and 5 positions. When the aryl group is phenyl and is substituted at one ring atom, the substituent is preferably present at the 4 position.

The substituent(s) present on the aryl group are preferably selected from halogen (e.g. F, Cl, Br), $C_{1-16}$ haloalkyl, $C_{1-16}$ alkyl, $C_{2-16}$ alkenyl, $C_{2-16}$ alkynyl, $C_{1-16}$ alkoxy, $C_{5-14}$ aryl, heteroaryl and arylalkyl. Examples of suitable haloalkyl groups include —$CF_3$, —$CF_2CF_3$ and —$CF_2CF_2CF_3$. Preferred alkyl groups are $C_{4-14}$ alkyl groups and more preferably $C_{6-12}$ alkyl groups. Examples of suitable alkyl groups include hexyl, heptyl, octyl, nonyl and decyl. Preferred alkenyl groups are $C_{4-14}$ alkenyl groups and more preferably $C_{6-12}$ alkenyl groups. Examples of preferred alkenyl groups include hexenyl, heptenyl, octenyl, nonenyl and decenyl. Preferred alkynyl groups are $C_{4-14}$ alkynyl groups and more preferably $C_{6-12}$ alkynyl groups. Examples of preferred alkynyl groups include hexadiynyl, heptdiynyl, octadiynyl, nonadiynyl and decadiynyl. Preferred alkoxy groups are $C_{4-14}$ alkoxy groups and more preferably $C_{6-12}$ alkoxy groups. Examples of suitable alkoxy groups include hexoxy, heptoxy, octoxy, nonoxy and decoxy. Examples of preferred aryl groups include phenyl and naphthyl. Examples of preferred heteroaryl groups include pyrrolyl, furanyl and thienyl. An example of a preferred arylalkyl group is benzyl.

Still more preferably the substituents present on the aryl group are selected from $C_{1-16}$ haloalkyl, $C_{1-16}$ alkyl and $C_{1-16}$ alkoxy. Yet more preferably the substituents present on the aryl group are $C_{1-16}$ alkyl. Examples of suitable alkyl groups include hexyl, heptyl, octyl, nonyl and decyl. Octyl is particularly preferred.

Yet more preferred compounds of formula (I) are those of formula (Ic):

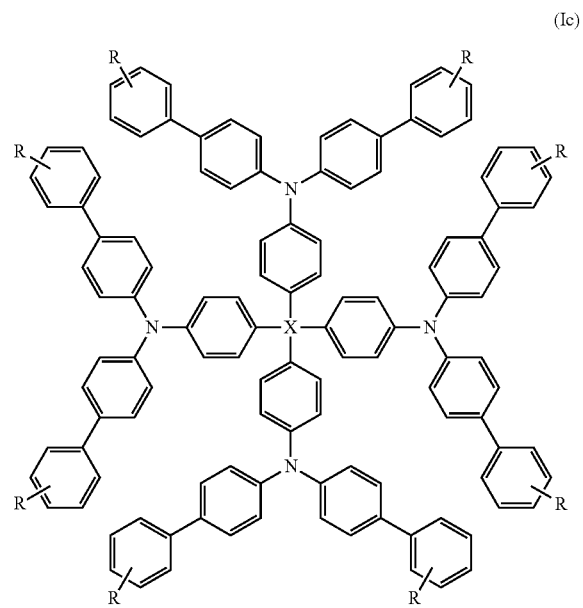

(Ic)

wherein X is as hereinbefore defined and R is selected from halogen, $C_{1-16}$ haloalkyl, $C_{1-16}$ alkyl, $C_{2-16}$ alkenyl, $C_{2-16}$ alkynyl, $C_{1-16}$ alkoxy, $C_{5-14}$ aryl, heteroaryl and arylalkyl. Still more preferably R is selected from $C_{1-16}$ haloalkyl, $C_{1-16}$ alkyl and $C_{1-16}$ alkoxy. Yet more preferably R is $C_{1-16}$ alkyl. Preferred alkyl groups are $C_{4-14}$ alkyl groups and more preferably $C_{6-12}$ alkyl groups. Examples of suitable alkyl groups include hexyl, heptyl, octyl, nonyl and decyl. Octyl is particularly preferred.

Still further preferred compounds of formula (I) are those of formula (Id):

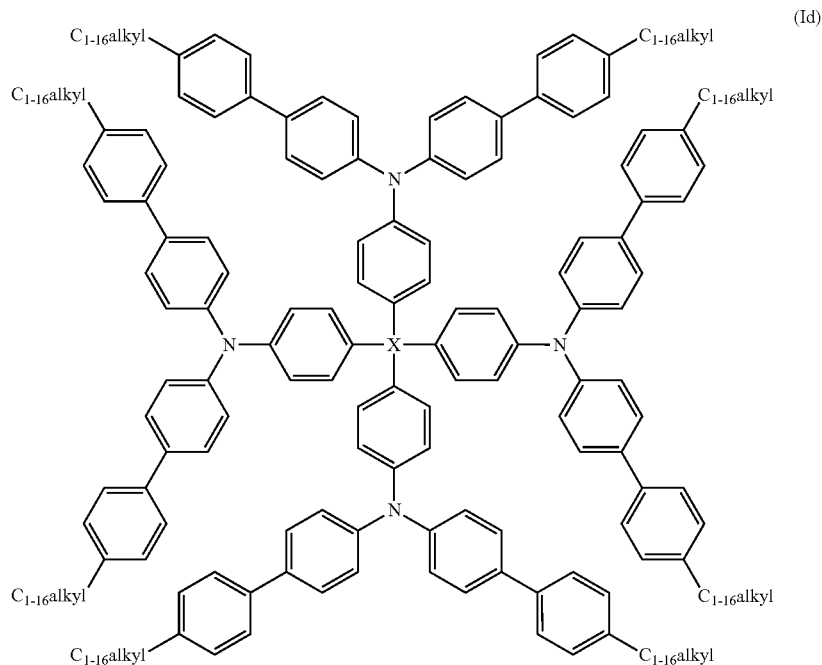
wherein X is as hereinbefore defined. More preferably X is Si.
Especially preferred compounds of the invention are compounds of formula (Ie), (If), (Ig) and (Ih) shown below:
-continued
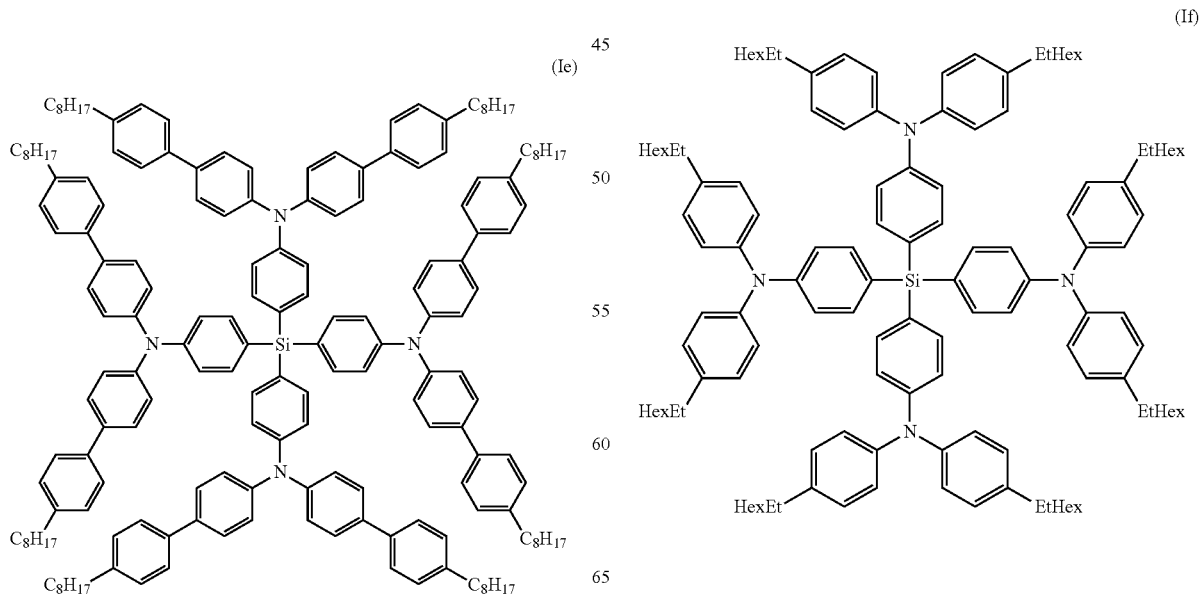

-continued

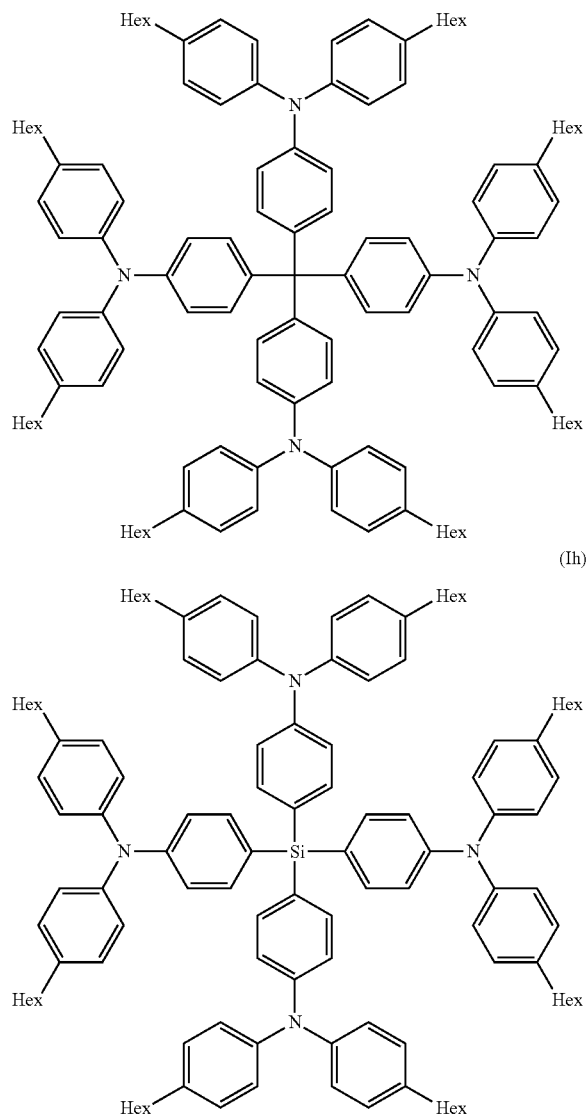

Without wishing to be bound by theory, it is believed that the light emitting layer generally present in optoelectronic devices such as polymer OLEDs perform two roles, light emission and charge carrier transport. The latter is necessary for supplying the holes and electrons which combine to produce excitons. Often, the host polymers in which the light emitting compound is present (see below) do predominantly support electron transport, but are not sufficiently hole transporting. In such cases, light emitting compounds such as phosphorescent iridium complexes can assume the additional role of hole transporting material, provided they are added at sufficiently high concentration. Advantageously it has now been found that the compounds of the present invention can function as hole transporting compounds when they are present in the light emitting layer of an optoelectronic device, and as a result the amount of light emitting compound present therein can be decreased. The optoelectronic properties of devices comprising a compound of the invention in combination with a light emitting compound have been found to be excellent thereby indicating that the compounds of the invention are excellent hole transporters. A significant advantage of such devices is that the compounds of the invention are much cheaper to manufacture than light emitting compounds such as phosphorescent iridium complexes therefore the cost of manufacturing the devices of the invention is significantly reduced.

Moreover it has also been discovered that the incorporation of the compounds of the present invention into the light emitting layer of an OLED does not adversely impact on the lifetime of the device. When additional compounds are incorporated into the light emitting layer of an optoelectronic device great care must be taken to prevent unwanted interaction between it and the charge transporting polymer and/or light emitting compound. Advantageously the HOMOs of the compounds of the present invention are localised on the centre of their structure. As a result the HOMOs are sterically hindered from interaction with the LUMO of, e.g. the electron transporting polymer. The different components of the light emitting layer are therefore each able to perform their functions individually without deleteriously impacting on each other.

The compounds of the present invention may be prepared by reacting a compound of formula (a) with a compound of formula (b) as hereinbefore defined. In preferred compounds of formula (a), X, a, b, c and d are as hereinbefore defined in relation to formula (I). In further preferred compounds of formula (a), halogen is bromine. In preferred compounds of formula (b), Z, E, W, e and z are as hereinbefore defined in relation to formula (II).

In preferred methods for making compounds of the present invention the reaction between the compound of formula (a) and the compound of formula (b) is a Buchwald-Harting amination. The skilled man in the art will readily be able to optimise the specific reactions conditions. Preferably the reaction is carried out in the presence of base, more preferably an alkoxide base and still more preferably $^t$BuONa. Preferably the reaction is carried out in the presence of a palladium catalyst, particularly a Pd(0) or Pd(II) catalyst. The catalyst preferably comprises ligands, particularly phosphine ligands. Preferably the reaction is carried out in the presence of a Fu salt.

The compounds of the present invention are preferably used in the manufacture of organic optoelectronic devices and more particularly in the manufacture of the active layer of such devices. Blends comprising the compounds of the present invention are preferably used for the manufacture of the active layer of such devices.

Preferred blends of the present invention comprise 10-60% wt of compound of formula (I), still more preferably 20 to 50% wt of compound of formula (I) and yet more preferably 30 to 45% wt of compound of formula (I).

Preferred blends of the present invention further comprise a light emitting compound. The light emitting compound is preferably a green emitter or a red emitter. Suitable red emitters are disclosed in WO2009/157424, WO2010/084977, GB2435194 and EP1449238, the contents of which are incorporated herein by reference. In preferred emitters, the metal is iridium.

More preferably the light emitting compound is a green emitter. Still more preferably the light emitting compound is a phosphorescent iridium complex.

Preferably the light emitting compound is a compound of formula (III):

wherein
M is a metal;
each of $L^1$, $L^2$ and $L^3$ is a ligand;

q is an integer;

r and s are each independently 0 or an integer; and the sum of (a. q)+(b. r)+(c.s) is equal to the number of coordination sites available on M, wherein a is the number of ligating sites on $L^1$, b is the number of ligating sites on $L^2$ and c is the number of ligating sites on $L^3$.

Heavy elements M induce strong spin-orbit coupling to allow rapid intersystem crossing and emission from triplet or higher states (phosphorescence). Suitable heavy metals M include: lanthanide metals (e.g. cerium, samarium, europium, terbium, dysprosium, thulium, erbium and neodymium) and d-block metals. Preferred d-block metals are those in rows 2 and 3 i.e. elements 39 to 48 and 72 to 80, in particular ruthenium, rhodium, palladium, rhenium, osmium, iridium, platinum and gold.

More preferably M is a d-block metal and still more preferably M is iridium.

Suitable ligands for the lanthanide metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure colour emission useful for display applications.

The d-block metals are particularly suitable for emission from triplet excited states. Ligating groups suitable for use with d-block elements include diketonates, in particular acetylacetonate (acac), triarylphosphines, pyridine, porphyrin or ligands comprising a bidentate group of formula (IV) as shown below:

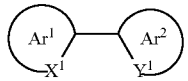
(IV)

wherein $Ar^1$ and $Ar^2$ may be the same or different and are independently selected from optionally substituted $C_{5-10}$ aryl or $C_{5-10}$ heteroaryl and/or are optionally fused together; and $X^1$ and $Y^1$ may be the same or different and are independently selected from carbon, sulfur or nitrogen.

Ligands comprising a bidentate group of formula (IV) are preferred. Ligands wherein $X^1$ is carbon and $Y^1$ is nitrogen are particularly preferred.

Preferred bidentate groups of formula (IV) are illustrated below:

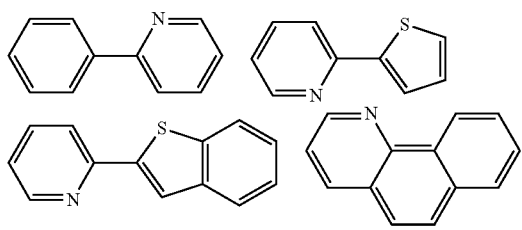

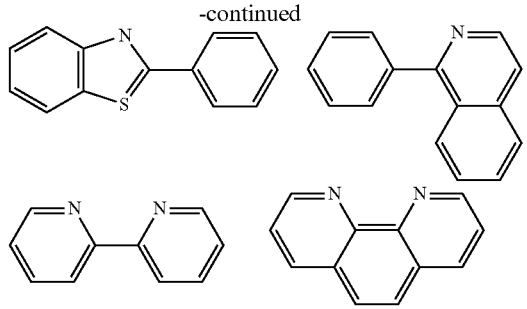

A particularly preferred bidentate group of formula (IV) is:

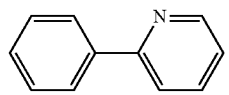 [SMILES: c1ccc(-c2ccccn2)cc1]

Each of $Ar^1$ and $Ar^2$ may carry one or more substituents. Two or more of these substituents may be linked to form a ring, for example an aromatic ring. Particularly preferred substituents include phenyl, which is optionally substituted with one or two optionally substituted phenyl groups, fluorine, trifluoromethyl, $C_{1-12}$ alkyl, $C_{1-12}$ alkoxy, carbazole, bromine, chlorine or iodine.

A particularly preferred light emitting compound is PGIA2 which has the structure shown below:

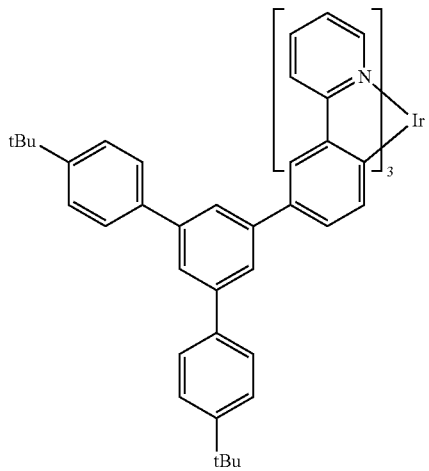

As an alternative to the presence of a light emitting compound, a light emitting complex may be chemically bound to a material present in the light emitting layer, e.g. a electron transporting polymer. A light emitting complex may be present for example as a substituent attached to the polymer backbone, incorporated as a repeat unit in the polymer backbone or provided as an end-group of the polymer as disclosed in, for example, EP1245659, WO 02/31896, WO03/18653 and WO 03/22908.

Preferred blends of the present invention comprise 5 to 20% wt of light emitting compound, more preferably 7.5 to 12.5% wt of light emitting compound and still more preferably about 10% wt of light emitting compound. This is much lower amounts than is generally present in OLEDs and is one of the advantages of the present invention.

Suitable light emitting compounds are commercially available from a range of suppliers. Alternatively light emitting compounds may be synthesised according to the methods disclosed in art.

In preferred blends of the present invention the weight ratio of compound of formula (I) to light emitting compound is 2:1 to 7:1, more preferably 3:1 to 6:1 and still more preferably 4:1 to 5:1.

Preferred blends of the present invention further comprise an electron transporting material. The electron transporting material may be polymeric or non-polymeric. Preferably, however, the electron transporting material is polymeric, i.e. an electron transporting polymer. The polymer also functions as a host or matrix in which the light emitting compound and compound of the invention are distributed.

Preferred electron transport polymers comprise a phenanthrene repeat unit, particularly a repeat unit of formula (N):

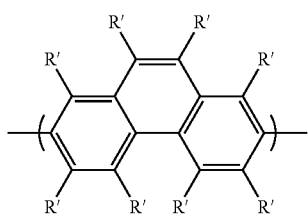

R' is on each occurrence, identical or different, H, a straight-chain, branched or cyclic alkyl chain having 1 to 40 C atoms, which may be substituted by R", and in which, in addition, one or more non-adjacent C atoms may be replaced by NR", O, S, O—CO—O, CO—O, —CR"=CR"—, and in which, in addition, one or more H atoms may be replaced by F, Cl, Br, I or CN, or an aromatic or heteroaromatic ring system having 2 to 40 C atoms, which may be substituted by one or more radicals R", or a combination of a plurality of these systems; the two radicals R' here may also form a further mono- or polycyclic, aliphatic ring system with one another;

R" is on each occurrence, identical or different, H, a straight-chain, branched or cyclic alkyl or alkoxy chain having 1 to 22 C atoms, in which, in addition, one or more non-adjacent C atoms may be replaced by NR''', O, S, O—CO—O, CO—O, or —CR'''=CR'''— and in which, in addition, one or more H atoms may be replaced by F, Cl, Br, I or CN, or an aryl, heteroaryl, aryloxy or heteroaryloxy group having 5 to 40 C atoms, which may also be substituted by one or more non-aromatic radicals R";

R''' is on each occurrence, identical or different, H or an aliphatic or aromatic hydrocarbon radical having 1 to 20 C atoms.

Preferred electron transporting polymers comprise a repeat unit of formula (O):

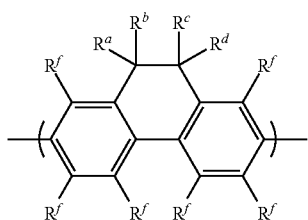

$R^a$ and $R^c$ is the same or different at each instance and is H, F, a straight-chain alkyl or alkoxy chain having 1 to 40 carbon atoms or a branched or cyclic alkyl or alkoxy chain having 3 to 40 carbon atoms, each of which may be substituted by $R^e$, and in which one or more non-adjacent carbon atoms may also be replaced by N—$R^e$, O, S, CO, O—CO—O, CO—O, —$CR^e$=$CR^e$—, Si($R^e$)$_2$, SO, SO$_2$ or PO($R^e$), and in which one or more hydrogen atoms may also be replaced by F, Cl, Br, I or CN, or an aromatic or heteroaromatic ring system which has 5 to 60 aromatic ring atoms and may also be substituted by one or more $R^e$ radicals; with the proviso that at least one of the two $R^a$ and $R^c$ radicals is not H; or $R^a$ and $R^c$ form a further mono- or polycyclic, aliphatic ring system with one another, which may be substituted by $R^e$ and in which one or more non-adjacent carbon atoms may also be replaced by N—$R^e$, O, S, CO, O—CO—O, CO—O, —$CR^e$=$CR^e$—, Si($R^e$)$_2$, SO, SO$_2$ or PO($R^e$), and in which one or more hydrogen atoms may also be replaced by F, Cl, Br, I or CN, or an aromatic or heteroaromatic ring system which has 5 to 60 aromatic ring atoms and may also be substituted by one or more $R^e$ radicals;

$R^b$ and $R^d$ is the same or different at each instance and is $R^a$;

$R^e$ is the same or different at each instance and is H, a straight-chain alkyl or alkoxy chain having 1 to 22 carbon atoms or a branched or cyclic alkyl or alkoxy chain having 3 to 22 carbon atoms, in which one or more non-adjacent carbon atoms may also be replaced by O, S, SO, SO$_2$, O—CO—O, CO—O, —CH=CH—, and in which one or more hydrogen atoms may also be replaced by F, Cl, Br, I or CN, or an aryl, heteroaryl, aryloxy or heteroaryloxy group which has 5 to 40 carbon atoms and may also be substituted by one or more non-aromatic $R^e$ radicals; in this structure, two or more of the $R^e$ radicals, together and/or with $R^a$ to $R^e$, may optionally form a ring system; and $R^f$ is the same or different at each instance and is the same as R' as defined above in relation to formula (N).

Preferred electron transporting polymers comprise a repeat unit of formula (P) which is an o-phenylene, m-phenylene or p-phenylene group, particularly a p-phenylene group. Preferably the phenylene repeating unit is substituted. Particularly preferably the phenylene repeat unit is of formula (P):

wherein
$R^1$ represents $C_{1-16}$ alkyl, $C_{1-16}$ alkoxy, $C_{1-16}$ alkylthio, $C_{5-14}$ aryl, $C_{5-14}$ aryloxy, $C_{5-15}$ arylthio, arylalkyl, arylalkoxy, arylalkylthio or a monovalent heterocyclic group; and
p is 0 or an integer.

In preferred repeat units of formula (P), p is 1 or 2, especially 2. When p is 2, the groups $R^1$ are preferably present at positions 2 and 5 or 3 and 6 of the ring. When p is greater than 1, the $R^1$ groups present may be the same or different.

In further preferred repeat units of formula (P), $R^1$ represents $C_{1-16}$ alkyl, more preferably $C_{1-10}$ alkyl and still more preferably $C_{1-6}$ alkyl, e.g. methyl or hexyl.

Two particularly preferred repeat units of formula (P) are shown below.

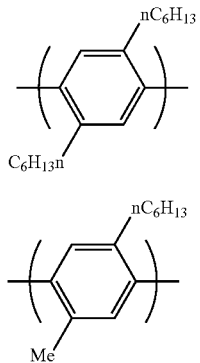

Repeat units of formula (P) may be incorporated into electron transporting polymers using monomers as described in EP2123691.

Further preferred electron transporting polymers comprise a repeat unit of formula (Q):

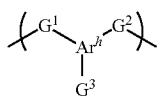

wherein $Ar^h$ comprises a substituted or unsubstituted heteroaryl group comprising 5 or 6 ring atoms; and each G is the same or different and independently comprises a substituted or unsubstituted $C_{5-14}$ aryl or $C_{5-14}$ heteroaryl group.

Representative examples of substituents that may be present on the aryl or heteroaryl groups are halide, cyano, $C_{1-16}$ alkyl, $C_{1-16}$ fluoroalkyl, $C_{1-16}$ alkoxy, $C_{1-16}$ fluoroalkoxy, $C_{5-14}$ aryl and $C_{5-14}$ heteroaryl.

In preferred repeat units of formula (Q) $Ar^h$ is a 6 membered ring. The ring preferably comprises 1, 2 or 3 heteroatoms. Particularly preferably the ring comprises 2 or 3 and especially 3 heteroatoms. Nitrogen is the preferred heteroatom. Especially preferably $Ar^h$ is a 1,3,5-triazine ring.

In further preferred repeat units of formula (Q) $G^1$ is an aryl group. Particularly preferably $G^1$ is a $C_6$ aryl group, e.g. phenyl. In further preferred repeat units of formula (Q) $G^2$ is an aryl group. Particularly preferably $G^2$ is a $C_6$ aryl group, e.g. phenyl. Still more preferably $G^1$ and $G^2$ are the same.

A particularly preferred repeat unit of formula (Q) is (Qi) as shown below:

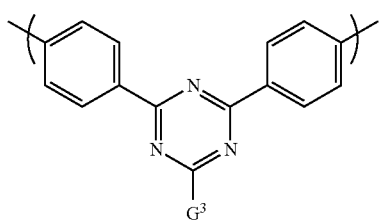

wherein $G^3$ is as defined above in relation to formula (Q).

Preferably $G^3$ is also a substituted or unsubstituted phenyl group. Preferably $G^3$ is substituted. Thus a further preferred repeat unit of formula (Q) is formula (Qii) shown below:

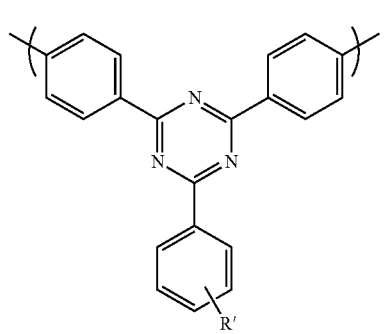

wherein R' is H or optionally substituted branched or linear $C_{1-16}$ alkyl or $C_{1-16}$ alkoxy, preferably alkyl. Particularly preferably R' is linear $C_{12}$ alkyl. Preferably R' is in the para position.

A particularly preferred repeat unit (Qiii) is shown below:

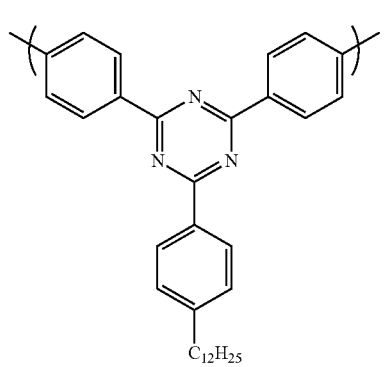

Repeat units of formula (Q) may be incorporated into electron transporting polymers using monomers as described in WO2002/083760.

Further preferred electron transporting polymers comprise a repeat unit of formula (R) which is an optionally substituted, 2,7-linked fluorene, most preferably a repeat units of formula (R) as shown below:

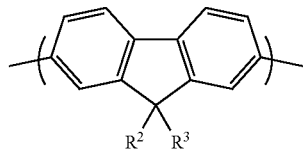

wherein $R^2$ and $R^3$ are independently selected from hydrogen or optionally substituted $C_{1-16}$ alkyl wherein one or more non-adjacent C atoms may be replaced with O, S, N, CO and —COO—, optionally substituted $C_{1-16}$ alkoxy, optionally substituted $C_{5-14}$ aryl, optionally substituted arylalkyl, optionally substituted $C_{5-14}$ heteroaryl and optionally substituted heteroarylalkyl. Optional substituents are preferably selected from the group consisting of $C_{1-16}$ alkyl or $C_{1-16}$ cycloalkyl wherein one or more non-adjacent C atoms may be replaced with O, S, N, C=O and —COO—, optionally substituted $C_{5-14}$ aryl, optionally substituted $C_{5-14}$ heteroaryl, $C_{1-16}$ alkoxy, $C_{1-16}$ alkylthio, fluorine, cyano and arylalkyl.

In preferred repeat units of formula (R) $R^2$ and $R^3$ are the same. In particularly preferred repeat units at least one and more preferably both of $R^2$ and $R^3$ comprise an optionally substituted $C_{1-16}$ alkyl or an optionally substituted $C_{5-14}$ aryl, e.g. a $C_6$ aryl. Preferred substituents of aryl groups are $C_{1-16}$ alkyl and still more preferably an unsubstituted $C_{1-16}$ alkyl group.

A particularly preferred repeat unit of formula (R) is shown below as formula (Ri):

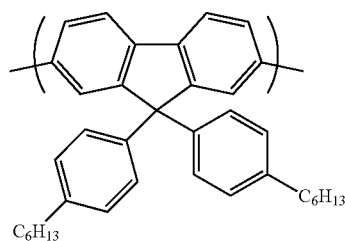

(Ri)

Repeat units of formula (R) may be incorporated into electron transporting polymers using monomers as described in WO2002/092723.

Further preferred electron transporting polymers comprise a repeat unit of formula (S):

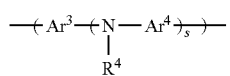

(S)

wherein $Ar^3$ and $Ar^4$ are optionally substituted $C_{5-14}$ aryl or $C_{5-14}$ heteroaryl groups, s is greater than or equal to 1, preferably 1 or 2, and $R^4$ is H or a substituent selected from $C_{1-16}$ alkyl, $C_{5-14}$ aryl or $C_{5-14}$ heteroaryl, most preferably aryl or heteroaryl. Any of the aryl or heteroaryl groups in the unit of formula S may be substituted. Preferred substituents include $C_{1-16}$ alkyl and $C_{1-16}$ alkoxy groups. Any of the aryl or heteroaryl groups in the repeat unit of Formula S may be linked by a direct bond or a divalent linking atom or group. Preferred divalent linking atoms and groups include O, S, substituted N and substituted C.

Particularly preferred repeat units of formula (S) are those of formula (Si-iii) shown below. Those of formula Siii are particularly preferred.

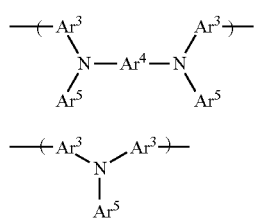

(Si)

(Sii)

(Siii)

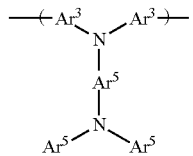

wherein $Ar^3$ and $Ar^4$ are as defined above; and $Ar^5$ is optionally substituted $C_{5-14}$ aryl or $C_{5-14}$ heteroaryl. When present, preferred substituents for $Ar^5$ include $C_{1-16}$ alkyl and $C_{1-16}$ alkoxy groups.

In preferred repeat units of formula (S) each of $Ar^3$, $Ar^4$ and $Ar^5$ are aryl, especially preferably $C_6$ aryl. Preferably $Ar^3$ and $Ar^4$ are unsubstituted. $Ar^5$ is preferably substituted. Preferred substituents are $C_{1-16}$ alkyl, more preferably $C_{1-6}$ alkyl.

A particularly preferred repeat unit of formula (S) is (Siv) shown below:

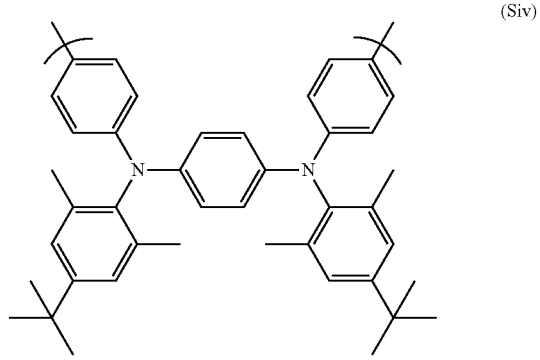

(Siv)

Repeat units of formula (S) may be incorporated into electron transporting polymers using monomers as described in WO2008/016090, WO2008/111658, WO2009/110642 and WO2010/013724.

Electron transporting polymers may optionally contain a light emitting unit. Preferred light emitting units are present as end caps in the polymer. Preferred light emitting units are of formula (T):

$$ML^1_q L^2_r L^3_s \qquad (T)$$

wherein M is a metal; each of $L^1$, $L^2$ and $L^3$ is a ligand; q is an integer; r and s are each independently 0 or an integer; and the sum of (a. q)+(b. r)+(c.s) is equal to the number of coordination sites available on M, wherein a is the number of ligating sites on $L^1$, b is the number of ligating sites on $L^2$ and c is the number of ligating sites on $L^3$.

In preferred monomers of formula (T) $L^1$, $L^2$ and $L^3$ are bidentate ligands. In further preferred monomers of formula (T) $L^1$, $L^2$ and $L^3$ are biaryl bidentate ligands, especially preferably biaryl bidentate ligands comprising one or more (e.g. one) heteroatoms. Preferably the heteroatom or heteroatoms are oxygen or nitrogen. In particularly preferred monomers of formula (T) $L^1$, $L^2$ and $L^3$ are biaryl bidentate nitrogen-containing ligands. The preferred metal M is iridium.

Particularly preferred light emitting units of formula (Ti) are those in which at least one of $L^1$, $L^2$ and $L^3$ are of the following structure:

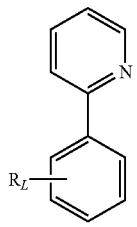

(Ti)

wherein $R_L$ is H or $Ar^6$ wherein $Ar^6$ is aryl, especially substituted $C_6$ aryl.

Preferred light emitting units of formula (Tii) are as follows:

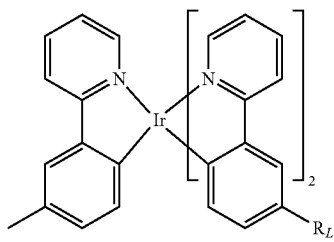

(Tii)

wherein $R_L$ is as defined above.

A particularly preferred light emitting of formula (Tiii) is shown below:

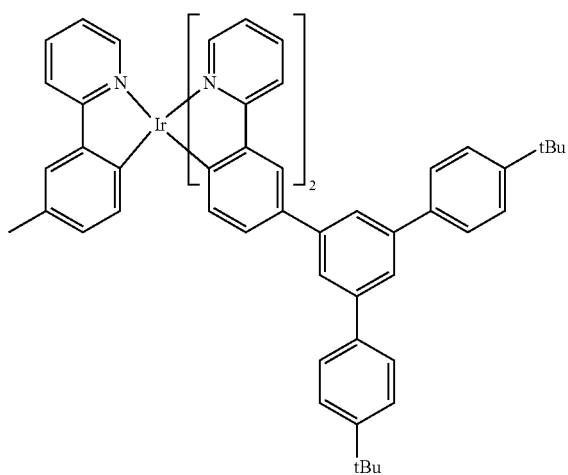

(Tiii)

Preferred electron transporting polymers for use in the present invention are block copolymers. Preferred block copolymers comprise a first block comprising repeat units of formulae (P) and (Q) and a second block comprising repeat units of formulae (P), (R) and (S). Particularly preferred block copolymers comprise a first block comprising repeat units of formulae (Pi), (Pii) and (Qiii) and a second block comprising repeating units of formulae (Pi), (Pii), (Ri) and (Siv).

Suitable electron transporting materials may be synthesised according to the methods disclosed in the art, e.g. in by Suzuki polymerisation as described in WO00/53656.

Preferred blends of the present invention comprise 30 to 70% wt of electron transporting material, more preferably 40 to 60% wt of electron transporting material and still more preferably 45 to 55% wt of an electron transporting material.

A preferred blend of the present invention comprises:
10-60% wt compound of formula (I);
30-70% wt electron transporting material; and
5-20% wt light emitting compound.

A further preferred blend of the present invention comprises:
20-50% wt compound of formula (I);
40-60% wt electron transporting material; and
7.5-12.5% wt light emitting compound.

A still further preferred blend of the present invention comprises:
30-45% wt compound of formula (I);
45-55% wt electron transporting material; and
about 10% wt light emitting compound.

When the compounds and blends of the present invention are used in the manufacture of organic optoelectronic devices, they are preferably dissolved to form solutions. The solutions may be used in solution processing techniques to form the active layer of such devices.

The solvent present in the solution is preferably an aromatic solvent. Suitable aromatic solvents are commercially available from a range of suppliers. Anhydrous grade solvents are typically selected. Such solvents are generally able to form solutions of compounds of the invention as well as electron transporting materials and light emitting compounds.

Preferably the aromatic solvent is a $C_{1-6}$ alkyl benzene. Optionally the $C_{1-6}$ alkyl benzene is further substituted. Representative examples of further substituents include $C_{1-6}$ alkyl, $OC_{1-6}$ alkyl and $C(O)OC_{1-6}$ alkyl, preferably $C_{1-6}$ alkyl. Di-$C_{1-6}$ alkyl substituted benzenes are preferred aromatic solvents.

Preferably the aromatic solvent is of formula (V):

(V)

wherein
$R^5$ is selected from $C_{1-6}$ alkyl and $OC_{1-6}$ alkyl, preferably $C_{1-6}$ alkyl; and
$R^6$ and $R^7$ are each independently selected from H and $C_{1-6}$ alkyl.

In preferred solvents of formula (I) $R^5$ is $C_{1-6}$ alkyl. In further preferred solvents $R^6$ is H. In still further preferred solvents $R^7$ is $C_{1-6}$ alkyl, preferably methyl. Yet more preferably $R^5$ is $C_{1-6}$ alkyl, preferably methyl, $R^6$ is H and $R^7$ is $C_{1-6}$ alkyl.

In other preferred solvents of formula (I) $R^5$ is $OC_{1-6}$ alkyl. In further preferred solvents $R^6$ is H. In still further preferred solvents $R^7$ is H. Yet more preferably $R^5$ is $OC_{1-6}$ alkyl, preferably methyl, $R^6$ is H and $R^7$ is H.

When the aromatic solvent is disubstituted, the substituents may be present in a [1,2], [1,3] or [1,4] substitution pattern. Preferably, however, the substituents are present in a [1,2] or ortho pattern. When the aromatic solvent is trisubstituted, the substituents are preferably present in a [1,3,5] substitution pattern.

Preferably the aromatic solvent is selected from the group consisting of toluene, o-xylene, m-xylene, p-xylene, anisole (or methoxybenzene) and mesitylene. Particularly preferably the aromatic solvent is selected from o-xylene, m-xylene or p-xylene. Still more preferably the aromatic solvent is o-xylene.

The concentration of solids (i.e. the compound of formula (I), the light emitting compound and the electron transporting polymer) in the solution is preferably in the range 0.6 to 3 wt % and more preferably 1.0 to 2.5 wt %. The concentration of the light emitting compound in the solids is preferably in the range 7.5 to 12.5 wt % and preferably about 10 wt %. The concentration of the electron transporting material in the solids is preferably in the range 40 to 60% wt and preferably 45 to 55 wt %. The concentration of the compound of formula (I) in the solids is preferably in the range 20 to 50% wt and preferably 30 to 45 wt %.

The compounds, blends and solutions of the present invention are preferably used in the manufacture of optoelectronic devices. Such devices comprise an anode, a cathode and an active organic layer in between the anode and cathode, wherein the active layer comprises a compound as hereinbefore described. The electrodes are preferably deposited by thermal evaporation. The active layer is preferably deposited by solution processing, e.g. spin coating. Optional additional layers, e.g. hole injection layer and interlayer are also preferably deposited by solution processing, e.g. spin coating.

Examples of optoelectronic devices that may be prepared using the compounds, blends and solutions of the present invention include organic light emitting diodes (OLEDs), organic photovoltaic devices (OPVs), organic photosensors, organic transistors and organic memory array devices.

The compounds, blends and solutions are particularly beneficial in the manufacture of OLEDs. In OLEDs the active organic layer is an organic light-emitting layer. Preferably the OLED comprises:
(i) a substrate;
(ii) an anode on said substrate;
(iii) a hole injection layer on said anode;
(iv) a light emitting layer on said hole injection layer; and
(v) a cathode on said light emitting layer,
wherein the light emitting layer comprises a compound or a blend as hereinbefore described.

Particularly preferred OLEDs additionally comprise an interlayer. Preferably the interlayer is in between the hole injection layer and the light emitting layer and/or in between the anode and the hole injection layer. A further optional layer is an electron transporting layer in between the light emitting layer and the cathode. Preferred OLEDS of the present invention comprise an interlayer in between the hole injection layer and the light emitting layer. Preferred OLEDs of the present invention do not comprise an electron transporting layer in between the light emitting layer and the cathode.

Preferred devices of the invention are also encapsulated to avoid ingress of moisture and oxygen. Conventional encapsulation techniques may be used.

The substrate may be any material conventionally used in the art such as glass or plastic. Optionally the substrate is pre-treated to improve adhesion thereto. Preferably the substrate is transparent. Preferably the substrate also has good barrier properties to prevent ingress of moisture or oxygen into the device.

The anode may comprise any material with a workfunction suitable for injection of holes into the light emitting layer. Preferably the anode is transparent. Representative examples of materials for use as a transparent anode include indium tin oxide (ITO) and indium zinc oxide (IZO). If the anode is not required to be transparent (e.g. if the cathode is transparent) then opaque conducting materials such as opaque metals may be used as the anode.

The anode may comprise a single layer or may comprise more than one layer. For example, the anode may comprise a first anode layer and an auxiliary conductive layer between the anode and the hole injection layer such as a layer of organic conductive material between the anode and the hole injection layer.

Preferably the anode is deposited on the substrate by thermal evaporation. The anode is preferably 20 to 200 nm thick and more preferably 10 to 100 nm thick.

The hole injection layer preferably comprises a conducting material. It assists hole injection from the anode into the light emitting layer. Representative examples of materials that may be used to form the hole injection layer include PEDOT:PSS, PANI (polyaniline), polypyrole, optionally substituted, doped poly(ethylene dioxythiophene) (PEDT), in particular PEDT doped with a charge-balancing polyacid such as polystyrene sulfonate (PSS) as disclosed in EP0901176 and EP0947123, polyacrylic acid or a fluorinated sulfonic acid, for example Nafion (R); polyaniline as disclosed in U.S. Pat. No. 5,723,873 and U.S. Pat. No. 5,798,170; and optionally substituted polythiophene or poly (thienothiophene). Other suitable materials are summarized in the book by Zigang Li and Hong Meng, Chapter 3.3 page 303-12. Examples of conductive inorganic materials include transition metal oxides such as $VO_x$, $MO_x$ and $RuO_x$ as disclosed in Journal of Physics D: Applied Physics (1996), 29(11), 2750-2753. Suitable materials for use as the hole injection layer are commercially available, e.g. from Plextronics Inc.

Preferably the hole injection layer is deposited by a solution-based processing method. Any conventional solution-based processing method may be used. Representative examples of solution-based processing methods include spin coating, dip coating, slot die coating, doctor blade coating and ink-jet printing. In preferred methods, however, depositing is by spin coating. The parameters used for spin coating the hole injection layer such as spin coating speed, acceleration and time are selected on the basis of the target thickness for the layer. After deposition, the hole injection layer is preferably annealed by heating, e.g. at 150 to 200° C. for 5 to 30 minutes in air.

The thickness of the hole injection layer is preferably 15 to 100 nm and more preferably 30 to 50 nm One preferred interlayer comprises a repeat unit of formula (P) as described above in relation to the charge transport polymer. Preferred repeat units are those described as preferred in relation to charge transport polymers, especially (Pi).

Repeat units of formula (P) may be incorporated into interlayer polymers using monomers as described in EP2123691.

Further preferred interlayers comprise a repeat unit of formula (U):

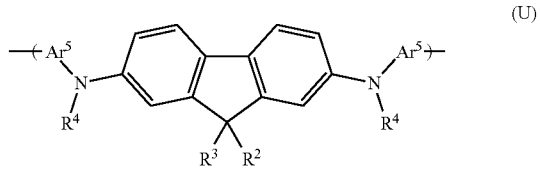

wherein $R^2$ and $R^3$ are independently selected from hydrogen or optionally substituted $C_{1-16}$ alkyl wherein one or more non-adjacent C atoms may be replaced with O, S, N, CO and —COO—, $C_{1-16}$ alkoxy, $C_{5-14}$ aryl, arylalkyl, $C_{5-14}$ heteroaryl and heteroarylalkyl; and $R^4$ and $Ar^5$ are independently selected from optionally substituted $C_{5-14}$ aryl or optionally substituted $C_{5-14}$ heteroaryl.

In preferred repeat units of formula (U) $R^2$ and $R^3$ are the same. In particularly preferred repeat units at least one and more preferably both of $R^2$ and $R^3$ comprise hydrogen or optionally substituted $C_{1-16}$ alkyl wherein one or more non-adjacent C atoms may be replaced with O, S, N, CO and —COO—, $C_{1-16}$ alkoxy, $C_{5-14}$ aryl, arylalkyl, $C_{5-14}$ heteroaryl and heteroarylalkyl. Particularly preferably $R^2$ and $R^3$ comprise $C_{1-16}$ alkyl, especially $C_{1-16}$ unsubstituted alkyl.

In further preferred repeat units of formula (U), $R^4$ is optionally substituted $C_{5-14}$ aryl, more preferably unsubstituted $C_{5-14}$ aryl and especially preferably phenyl.

In further preferred repeat units of formula (U), $Ar^5$ is optionally substituted $C_{5-14}$ aryl, more preferably unsubstituted $C_{5-14}$ aryl and especially preferably phenyl.

A particularly preferred repeat unit of formula (Ui) is shown below:

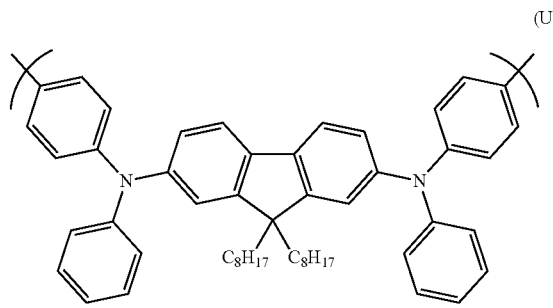

(Ui)

Repeat units of formula (U) may be incorporated into interlayer polymers using monomers as described in WO2005/049546.

Further preferred interlayer polymers comprise a repeat unit of formula (X):

(X)

wherein $Ar^7$ and $Ar^8$ represent $C_{5-14}$ aryl or $C_{5-14}$ heteroaryl and X' is a crosslinkable or thermosettable group.

In preferred units of formula (X) $Ar^7$ and $Ar^8$ are the same. In particularly preferred repeat units $Ar^7$ and $Ar^8$ comprise optionally substituted $C_{5-14}$ aryl. When present, preferred substituents for $Ar^7$ and $Ar^8$ include $C_{1-16}$ alkyl and $C_{1-16}$ alkoxy groups. Especially preferred $Ar^7$ and $Ar^8$ groups are unsubstituted $C_6$ aryl.

Examples of crosslinkable or thermosettable group X' in repeat unit X include moieties containing a double bond, a triple bond, a precursor capable of in situ formation of a double bond, or an unsaturated heterocyclic group. In preferred repeat units of formula (X) the crosslinkable or thermosettable group X' contains a precursor capable of in situ formation of a double bond. More preferably X' contains a benzocyclobutanyl group. Especially preferred X' groups comprise a $C_{5-12}$ aryl group substituted with a benzocyclobutanyl group, particularly preferably $C_6$ aryl substituted with a benzocyclobutanyl group.

A particularly preferred repeat unit (Xi) is shown below:

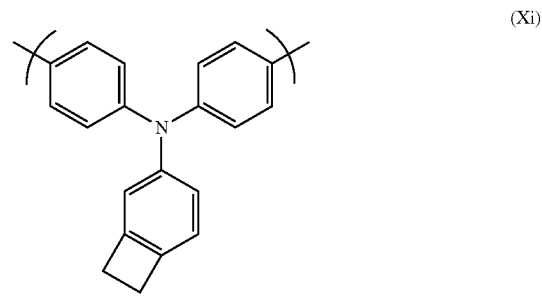

(Xi)

Repeat units of formula (X) may be incorporated into interlayer polymers using monomers as described in WO2005/052027.

Further prepared interlayer polymers comprise a repeat unit of formula (R), as defined above in relation to the charge transporting polymer.

A particularly preferred repeat unit of formula (R) for use in the interlayer polymers of the invention is (Rii) as shown below:

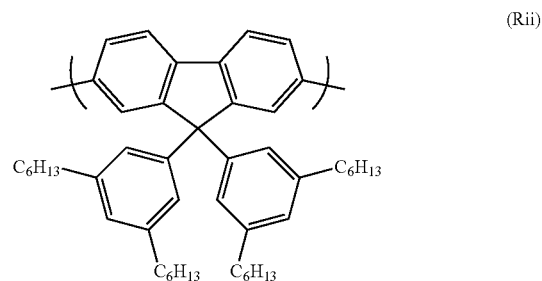

(Rii)

A further preferred repeat unit of formula (R) for use in the interlayer polymers of the invention is (Riii) as shown below:

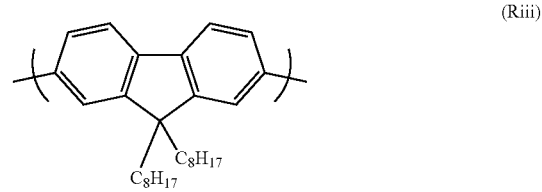

(Riii)

A yet further preferred repeat unit of formula (R) for use in the interlayer polymers of the invention is (Riv) as shown below:

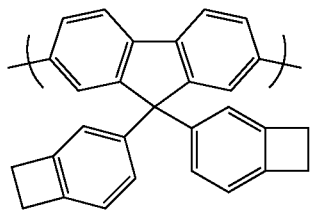
(Riv)

Suitable interlayer materials may be synthesised according to the methods disclosed in the art, for example, in WO2005/049546, EP2123691, WO2005/052027 and WO00/53656.

One preferred interlayer polymer of the present invention comprises repeat units of formulae (P), (U) and (X). Particularly preferred polymers comprise repeat units of formulae (Pi), (Ui) and (Xi).

One preferred interlayer polymer of the present invention comprises:
10-90% wt repeat unit (Pi);
10-90% wt repeat unit (Ui); and
1-50 wt % repeat unit (Xi).

A further preferred interlayer polymer of the present invention comprises:
30-60% wt repeat unit (Pi);
30-60% wt repeat unit (Ui); and
1-20 wt % repeat unit (Xi).

A still further preferred interlayer polymer of the present invention comprises:
40-55% wt repeat unit (Pi);
40-50% wt repeat unit (Ui); and
5-10 wt % repeat unit (Xi).

One further preferred interlayer polymer of the present invention comprises repeat units of formulae (R), (U) and (Riv). Particularly preferred polymers comprise repeat units of formulae (Rii), (Riii), (Ui) and (Riv).

One preferred interlayer polymer of the present invention comprises:
10-90% wt repeat unit (Rii);
10-90% wt repeat unit (Riii);
1-20% wt (Ui); and
1-20% wt (Riv).

A further preferred interlayer polymer of the present invention comprises:
30-60% wt repeat unit (Rii);
20-50% wt repeat unit (Riii);
5-20% wt (Ui); and
1-10% wt (Riv).

A still further preferred interlayer polymer of the present invention comprises:
40-55% wt repeat unit (Rii);
20-35% wt repeat unit (Riii);
10-15% wt (Ui); and
5-10% wt (Riv).

Preferably the interlayer is deposited by a solution-based processing method. Any conventional solution-based processing method may be used. Representative examples of solution-based processing methods include spin coating, dip coating, slot die coating, doctor blade coating and ink-jet printing. In preferred methods, however, depositing is by spin coating. The parameters used for spin coating the interlayer such as spin coating speed, acceleration and time are selected on the basis of the target thickness for the layer.

After deposition, the interlayer is preferably crosslinked by heating, e.g. at 150 to 200° C. for 30 to 120 minutes in a glove box.

The thickness of the interlayer is preferably 5 to 50 nm and more preferably 10 to 40 nm The light emitting layer is preferably prepared using a solution as hereinbefore described. More preferably the light emitting layer is prepared by depositing a solution as hereinbefore defined on the anode or, when present the hole injection layer or interlayer. Any conventional solution-based processing method may be used. Representative examples of solution-based processing methods include spin coating, dip coating, slot die coating, doctor blade coating and ink-jet printing. In preferred methods, however, depositing is by spin coating. The parameters used for spin coating the light emitting layer such as spin coating speed, acceleration and time are selected on the basis of the target thickness for the light emitting layer. After depositing the light emitting layer is preferably dried, e.g. at 100-150° C. in a glove box.

The thickness of the light emitting layer is preferably 50 to 350 nm and more preferably 75 to 150 nm.

The cathode may comprise any material having a workfunction allowing injection of electrons into the light-emitting layer. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977. The cathode may consist of a single material such as a layer of aluminium. Alternatively, it may comprise a plurality of metals, for example a bilayer or trilayer of a low workfunction material and a high workfunction material such as calcium and aluminium as disclosed in WO 98/10621; elemental barium as disclosed in WO 98/57381, Appl. Phys. Lett. 2002, 8 1(4), 634 and WO 02/84759; or a thin layer of metal compound, in particular an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. A particularly preferred cathode comprises a layer of NaF, a layer of Al and a layer of Ag.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

Preferably the cathode is deposited on the substrate by thermal evaporation. The cathode is preferably 100 to 400 nm thick and more preferably 200 to 350 nm thick.

Suitable encapsulants include a sheet of glass, films having suitable barrier properties such as silicon dioxide, silicon monoxide, silicon nitride or alternating stacks of polymer and dielectric as disclosed in, for example, WO 01/81649 or an airtight container as disclosed in, for example, WO 01/19142. In the case of a transparent cathode device, a transparent encapsulating layer such as silicon monoxide or silicon dioxide may be deposited to micron levels of thickness, although in one preferred embodiment the thickness of such a layer is in the range of 20-300 nm.

A material for absorption of any atmospheric moisture and/or oxygen that may permeate through the substrate or encapsulant may optionally be disposed between the substrate and the encapsulant.

Preferred devices of the present invention have one or more of the following structural characteristics:

| | |
|---|---|
| Substrate: | Glass surface |
| Anode: | ITO |
| Anode thickness: | 10 to 100 nm |
| Hole injection layer: | Polymeric charge conducting material |
| Hole injection layer thickness: | 30-50 nm |
| Interlayer: | Polymer comprising repeat units (Pi), (Ui) and (Xi) or (Rii), (Riii), (Ui) and (Riv). |
| Interlayer thickness: | 10 to 40 nm |
| Light emitting layer: | Blend of invention |
| Light emitting layer thickness: | 75 to 150 nm |
| Cathode: | NaF/Al/Ag |
| Cathode thickness: | 200 to 350 nm |

Organic optoelectronic devices of the present invention which comprise a light emitting layer comprising 10% wt light emitter and a compound of the invention are characterised by having a higher EQE at 1000 cd/m$^2$ than an identical device which comprises a light emitting layer comprising 10% wt light emitter but no compound of the invention. Still more preferably the devices of the present invention which comprise a light emitting layer comprising 10% wt light emitter and 40% wt of compound of the invention are characterised by having a 10% and more preferably a 20% higher EQE at 1000 cd/m$^2$ than an identical device which comprises a light emitting layer comprising 10% wt light emitter but no compound of the invention.

Organic optoelectronic devices of the present invention which comprise a light emitting layer comprising 10% wt light emitter and 50% wt compound of the invention are characterised by having a substantially identical EQE at 1000 cd/m$^2$ to an identical device which comprises a light emitting layer comprising 40% wt light emitter but no compound of the invention. Still more preferably the devices of the present invention which comprise a light emitting layer comprising 10% wt light emitter and 50% wt compound of the invention are characterised by having an EQE at 1000 cd/m$^2$ that is at least 85% and more preferably at least 90% of the EQE of an identical device which comprises a light emitting layer comprising 40% wt light emitter but no compound of the invention.

Organic optoelectronic devices of the present invention which comprise a light emitting layer comprising 4.4% wt light emitter and 39.1% wt compound of the invention are characterised by having a longer lifetime at 1000 cd/m$^2$ than an identical device which comprises a light emitting layer comprising 5% wt light emitter but no compound of the invention. Still more preferably the devices of the present invention which comprise a light emitting layer comprising 4.4% wt light emitter and 39.1% wt compound of the invention are characterised by having a 2 times and more preferably a 3.5 times longer lifetime at 1000 cd/m$^2$ than an identical device which comprises a light emitting layer comprising 5% wt light emitter but no compound of the invention.

Organic optoelectronic devices of the present invention which comprise a light emitting layer comprising 10% wt light emitter and 40% wt compound of the invention are characterised by having a lower drive voltage at 1000 cd/m$^2$ than an identical device which comprises a light emitting layer comprising 10% wt light emitter but no compound of the invention. Still more preferably the devices of the present invention which comprise a light emitting layer comprising 10% wt light emitter and 40% wt compound of the invention are characterised by having a 10%, and more preferably 14%, lower drive voltage at 1000 cd/m$^2$ than an identical device which comprises a light emitting layer comprising 10% wt light emitter but no compound of the invention.

Organic optoelectronic devices of the present invention which comprise a light emitting layer comprising 10% wt light emitter and 40% wt compound of the invention are characterised by having a higher current density at 4 V than an identical device which comprises a light emitting layer comprising 10% wt light emitter but no compound of the invention. Still more preferably the devices of the present invention which comprise a light emitting layer comprising 10% wt light emitter and 40% wt compound of the invention are characterised by having a 1.5 times and more preferably 2 times higher current density at 4 V than an identical device which comprises a light emitting layer comprising 10% wt light emitter but no compound of the invention.

DETAILED DESCRIPTION OF THE INVENTION

Figure 1A:
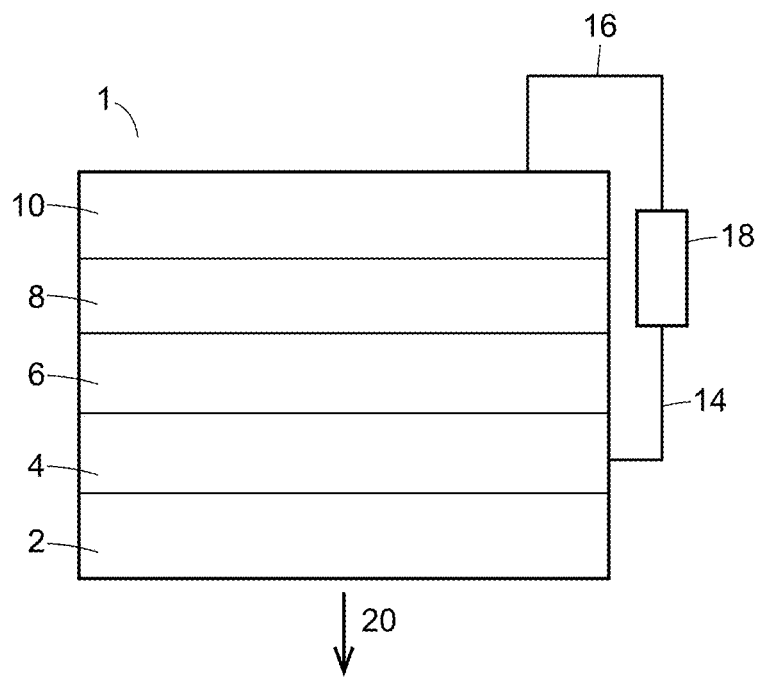
FIG. 1A is a schematic of a typical bottom emitter OLED.

A cross-section through a basic structure of a typical OLED 1 is shown in FIG. 1A. A glass or plastic substrate 2 supports a transparent anode layer 4 comprising, for example, indium tin oxide (ITO) on which is deposited a hole injection layer 6, a light emitting layer 8 and a cathode 10. The light emitting layer 8 comprises a blend of the present invention. The hole injection layer 6, which helps match the hole energy levels of the anode layer 4 and the light emitting layer 8, comprises a conductive transparent polymer. Cathode 10 comprises a bilayer of silver and aluminium and includes an additional layer of sodium fluoride for improved electron energy level matching. Contact wires 14 and 16 to the anode and the cathode respectively provide a connection to a power source 18.

In so-called "bottom emitter" devices, the multi-layer sandwich is deposited on the front surface of a planar glass substrate, with the reflecting electrode layer, usually the cathode, furthest away from the substrate, whereby light generated internally in the light emitting layer is coupled out of the device through the substrate. An example of a bottom emitter 1a is shown in FIG. 1A, where light 20 is emitted through transparent anode 4 and substrate 2 and the cathode 10 is reflective.

Figure 1B:
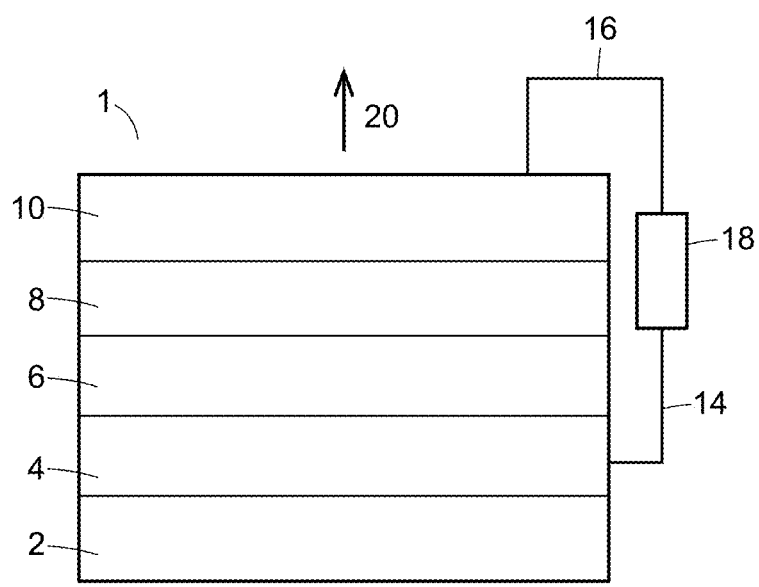
FIG. 1B is a schematic of a typical top emitter OLED.

Conversely, in a so-called "top emitter", the multi-layer sandwich is disposed on the back surface of the substrate 2, and the light generated internally in the light emitting layer 8 is coupled externally through a transparent electrode layer 10 without passing through the substrate 2. An example of a top emitter is shown in FIG. 1B. Usually the transparent electrode layer 10 is the cathode, although devices which emit through the anode may also be constructed. The cathode layer 10 can be made substantially transparent by keeping the thickness of cathode layer less than around 50-100 nm, for example.

EXAMPLES

Materials

The substrate is glass obtained from Corning.

The anode is indium tin oxide (ITO). The ITO was thermally deposited on the above substrate. Alternative substrates comprising ITO may be obtained from, e.g. Praezisions Glas & Optik GmbH.

The hole injection layer (HIL) is Plexcore© OC AQ-1200, available from Plextronics Inc.

The interlayer (IL) is described below.

The light emitting layer was prepared as described below.

The cathode is NaF—Al—Ag. These were prepared by sequential thermal evaporation or sputtering of the materials listed.

Interlayers

Interlayer 1 comprises monomers (Pi), (Ui) and (Xi). Interlayer 1 was polymerised by Suzuki polymerisation as described in WO0053656

Interlayer 2 comprises monomers (Rii), (Riii), (Ui) and (Riv). Interlayer 2 was polymerised by Suzuki polymerisation as described in WO0053656.

Preparation of a Blend for Making the Light Emitting Layer

The blend comprises an electron transporting polymer (ETP), a green iridium emitter (PGIA2) and a compound of formula (I). The electron transporting polymer was prepared by polymerisation as described in WO00/53656. It comprises repeating units shown below in the ratio $(Pi_1\text{-}Pii_5\text{-}Qiii_{10})\text{-}b\text{-}(Pi_{22}\text{-}Pii_{22}\text{-}Ri_{39}\text{-}Siv_1)$ wherein b indicates block in a block copolymer.

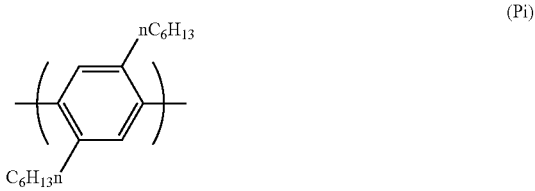
(Pi)

(Pii)

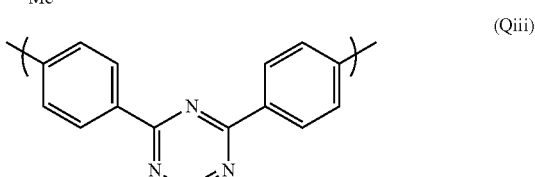
(Qiii)

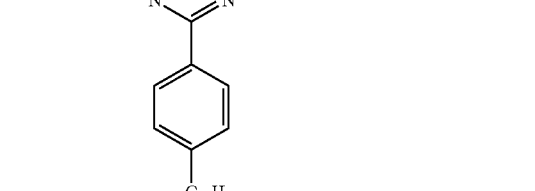

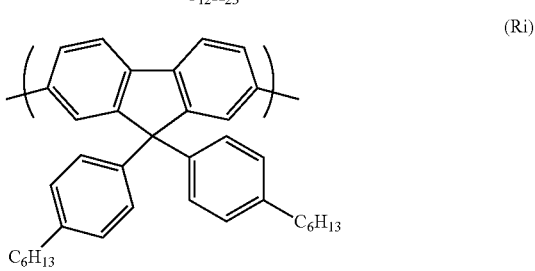
(Ri)

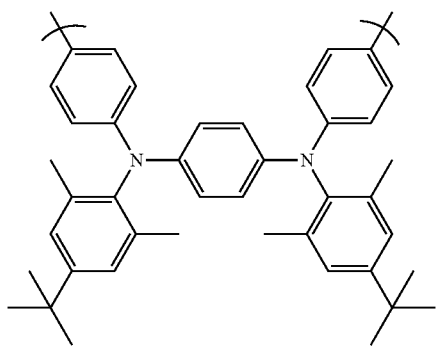
(Siv)

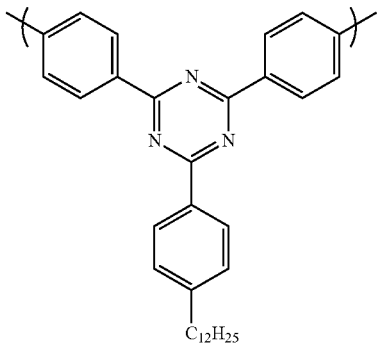
(Qiii)

The green iridium emitter has the formula shown below. It may be synthesised according to procedures known in the art, e.g. from WO2002/066552 or US2011/272686.

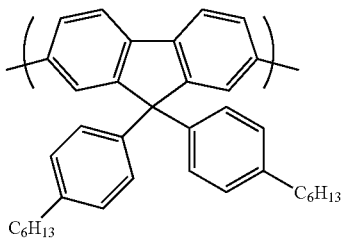
(Ri)

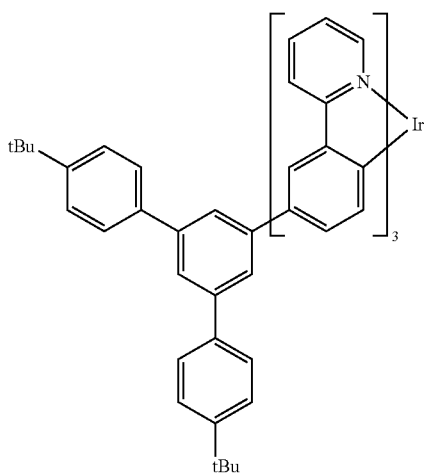
PGIA2

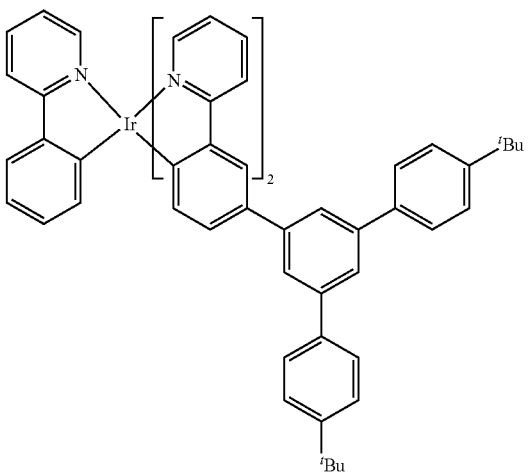
(Tiii)

An alternative blend of the present invention comprises a polymer which additionally incorporates a light emitting monomer. The polymer was prepared by polymerisation as described in GB2435194. It comprises repeating units shown below in the ratio $(Pi_1\text{-}Pii_5\text{-}Qiii_{10})\text{-}b\text{-}(Pi_{22}\text{-}Pii_{22}\text{-}Ri_{38}\text{-}Tiii_2)$

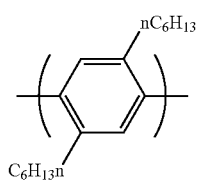
(Pi)

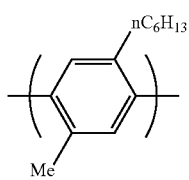
(Pii)

The blend was prepared by charging Pi, Pii, Qiii, Ri and Tiii in the required relative amounts to a reaction vessel, followed by replacing the atmosphere in the reaction vessel with nitrogen gas. To this mixture was added THF (which was previously deoxygenated by purging with argon) followed by bis-(1,5-cyclooctadiene)nickel(0) (Ni(cod)$_2$). The reaction mixture was agitated under a nitrogen atmosphere at room temperature for 30 minutes, then at 60° C. for 3.3 hours. The reaction mixture was then cooled to room temperature and poured into a 25 wt % solution of ammonium chloride or hydroxide in 1:1 MeOH:H$_2$O. Precipitation was induced by agitation over 2 hours, and the precipitate collected by filtration and dried under reduced pressure. The precipitate was then redissolved in toluene, filtered to remove insoluble impurities, and the solution passed through an alumina column followed by washing with 1N HCl, 2.5 wt % aqueous ammonium chloride or hydroxide then water. The purified solution was then poured into methanol to precipitate the polymer, which was collected by filtration and dried under reduced pressure.

The compounds of formulae (Ie), (If) and (Ig) of the formula shown hereinbefore were synthesised according to the scheme shown below.
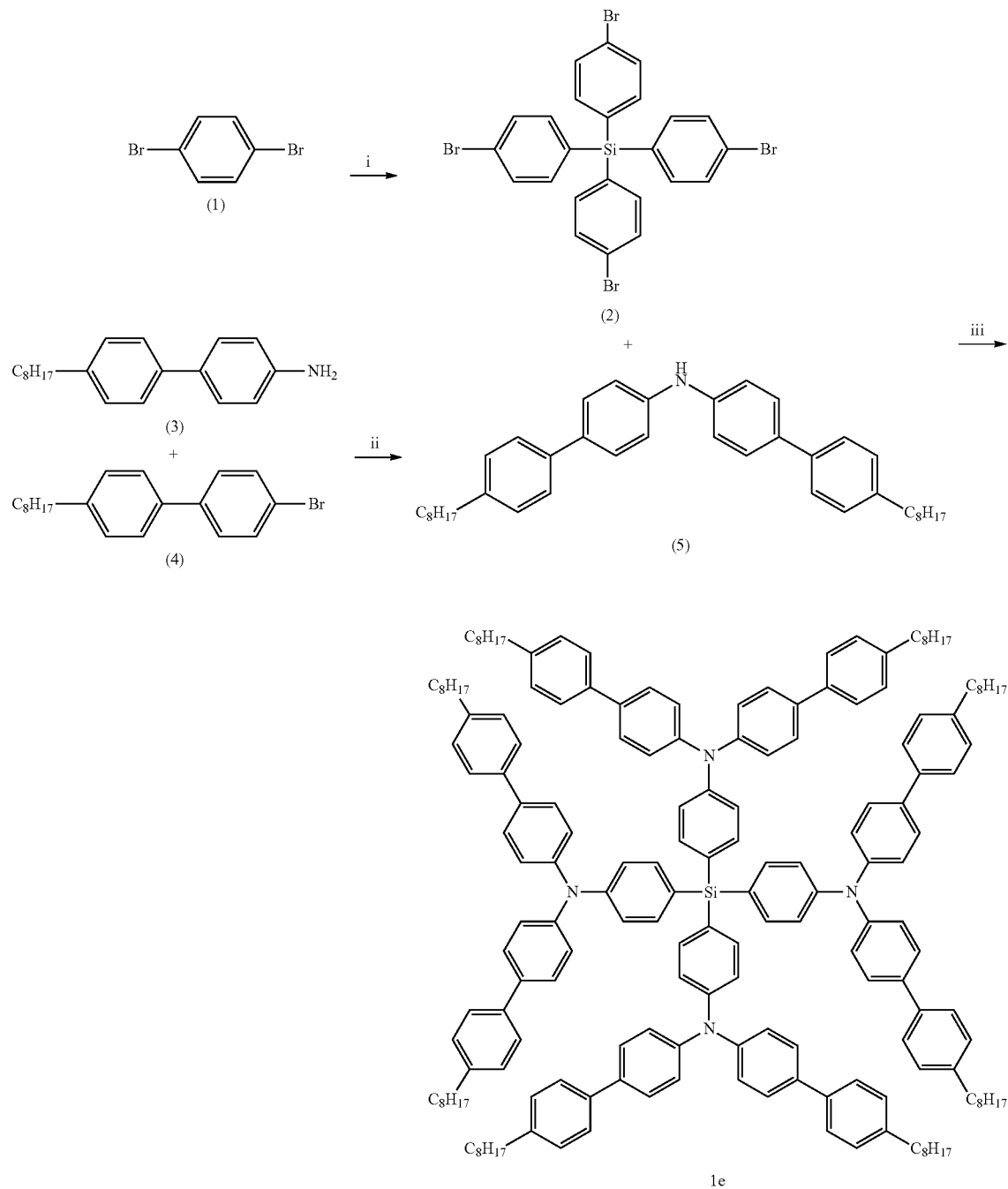
Scheme 1
i. nBuLi, SiCl$_4$, Et$_2$O, -78° C. to -10° C., 1 hr;
ii. Pd$_2$(dba)$_3$, $^t$Bu$_3$P$^+$HBF$_4^-$, $^t$BuONa, Toluene, 90° C., 5 hrs;
iii. Pd$_2$(dba)$_3$, $^t$Bu$_3$P$^+$HBF$_4^-$, $^t$BuONa, Toluene, 90° C.

Synthesis

Tetrakis-(4-bromophenyl)silane (2)

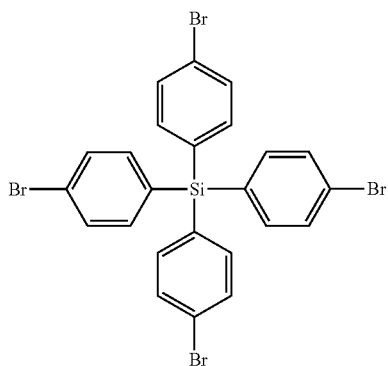

(2)

n-BuLi (89 ml, 0.22 mol, 2.5M) was added dropwise to a solution of 1,4-dibromobenzene (50 g, 0.21 mol) in anhydrous diethyl ether (500 ml) at −78° C. under nitrogen. After stirring for 30 min, the reaction mixture was warmed to −10° C. and SiCl$_4$ (9.0 g, 0.05 mol) was added dropwise. After a further 15 min, the reaction mixture was quenched with HCl (250 ml, 1.5M) and ethyl acetate (500 ml) was added. The organic phase was separated, washed with NaCl (750 ml), dried over sodium sulphate, filtered and concentrated. The crude oil was purified by column chromatography (silca-gel 230-400 mesh, hexane) and recrystalization (EtOAc) to give silane (2) as a while solid (24 g, 17% yield).

$^1$H-NMR 400 MHz, CDCl$_3$: δ 7.36 (d, J=8.2 Hz, 8H), 7.56 (d, J=8.2 Hz, 8H).

$^{13}$C NMR 75 MHz, CDCl$_3$: 125.38, 131.37, 131.41, 137.54.

GCMS: 652M$^+$, 573, 495; HPLC: 99.51%.

Bis-4-(4'-n-octyl)biphenylamine (5)

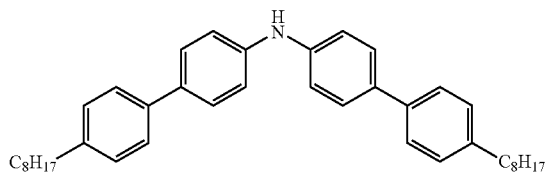

(5)

A solution of 4'-n-octyl-4-aminobiphenyl (3) (100 g, 0.36 mol), 4'-n-octyl-4-bromobiphenyl (4) (147 g, 0.43 mol), tBuONa (102 g, 1.07 mol) in toluene (3 L), was purged with nitrogen for 30 min. Pd$_2$(dba)$_3$ (13 g, 0.01 mol) and $^t$Bu$_3$P$^+$HBF$_4^-$ (6.1 g, 0.02 mol) were added and the reaction mixture heated at 90° C. for 5 h. The resulting dark brown mixture was filtered through celite at 80° C. and washed with ethyl acetate (2 L). The filtrate was washed with water (2 L), NaCl (2 L), dried over sodium sulphate, filtered and concentrated. The crude material was triturated with diethyl ether (2 L) to give bis-4-(4'-n-octyl)biphenylamine (5) as a yellow solid (92 g, 47% yield).

$^1$H NMR 300 MHz, CDCl$_3$: δ 0.83 (t, J=6.4 Hz, 6H), 1.25-1.45 (m, 20H), 1.55-1.68 (m, 4H), 2.62-2.73 (m, 4H), 7.05-715 (m, 1H), 7.24 (d, J=8.0 Hz, 8H), 7.44-7.62 (m, 8H).

LCMS: 546M$^+$;

HPLC: 98.38%.

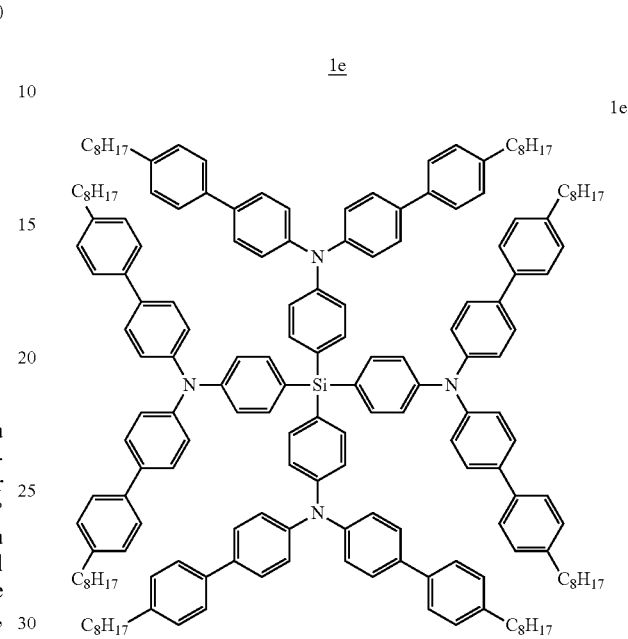

1e

A solution of tetrakis-(4-bromophenyl)-silane (2) (25 g, 0.04 mol), bis-4-(4'-n-octyl)biphenylamine (5) (93.3 g, 0.17 mol), tBuONa (21.9 g, 0.23 mol) in toluene (2.25 L) was degassed by purging with nitrogen for 30 min. Pd2(dba)3 (1.8 g, 0.002 mol) and $^t$Bu$_3$P$^+$HBF$_4^-$ (0.8 g, 0.003 mol) were added and the reaction mixture was heated at 90° C. 16 h. The resulting dark mixture was filtered through celite and washed with methyl tbutyl ether (2 L). The filtrate was washed with water (2 L), NaCl (2 L), dried over sodium sulphate, filtered and concentrated. The crude material was purified by column chromatography (silca 230-400 mesh, 1% EtOAc:hexane) and recrystalization (EtOAc, 850 ml) to give (1e) as a white solid (38 g, 40% yield).

$^1$H NMR 400 MHz, CDCl$_3$: δ 0.89 (t, J=6.6 Hz, 24H), 1.25-1.45 (m, 80H), 1.62-1.68 (m, 16H), 2.64 (t, J=7.6 Hz, 16H), 7.17 (d, J=8.4 Hz, 8H), 7.21-7.25 (m, 32H), 7.49-7.53 (m, 40H).

$^{13}$C NMR 100 MHz, CDCl$_3$: 14.10, 22.67, 29.27, 29.39, 29.49, 31.48, 31.89, 35.61, 122.23, 125.02, 126.55, 127.71, 128.80, 135.96, 137.32, 137.92, 141.73, 146.37, 148.68

HRMS: 2511M$^+$; HPLC: 99.71%.

Derivatives 1 f, g and h can be synthesized in an analogous fashion using a similar approach to that described for 1e.

The blends for the light emitting layer were prepared by weighing out appropriate amounts of each of electron transporting (host) polymer, compound of formula (I) and light emitting compound. These materials were then combined in a vial, solvent was added and the vial placed on a roller overnight to dissolve the solids. Prior to device fabrication, the combined solution is filtered through PTFE syringe filters with 0.45 micron pore size.

Preparative Example for the Fabrication of Organic Light Emitting Diodes

Figure 2:
FIG. 2 is a schematic of an OLED prepared according to the examples of the present invention.
Figure 3:
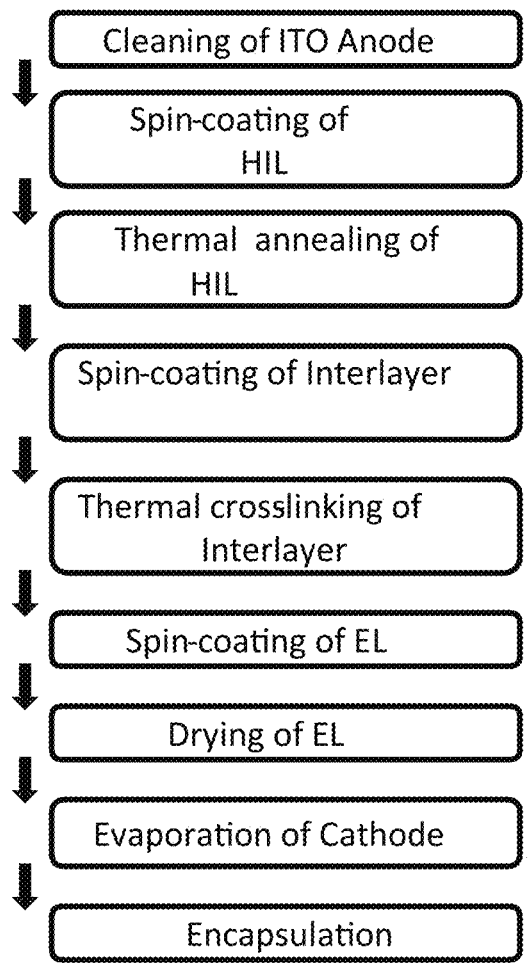
FIG. 3 is a flow diagram of the method used to prepare the OLEDs in the examples of the present invention.

A device having the structure shown in FIG. 2 was prepared. The preparative process used is set in the flow diagram in FIG. 3.

(i) Depositing and Cleaning of ITO Anode

The ITO anode was deposited on a glass substrate by thermal deposition. The ITO anode was then cleaned in a UV-ozone generator (15 minutes in a USHIO UV ozone generator). The thickness of the anode is 45 nm.

(ii) Spin Coating and Thermal Annealing of HIL

The HIL was deposited by spin-coating Plexcore© OC AQ-1200, available from Plextronics, Inc., from water in air, to a thickness of 35 nm. The HIL was thermally annealed at 170° C. for 15 minutes in air.

(iii) Spin Coating and Cross-Linking of IL

The IL was deposited by spin-coating interlayer 1 or interlayer 2, from a 0.6 wt % concentration solution in o-xylene. Interlayer 1 is present in the devices of example 1, table 1a; example 2, table 2a; example 3, table 3a; and example 4. Interlayer 2 is present in the devices of example 1, table 1b; example 2, table 2b; and example 3, table 3b. The IL was thermally cross-linked at 180° C. for 60 minutes in a glove box. The final IL has a thickness of 22 nm.

(iv) Spin Coating of Light Emitting Layer

The light emitting layer comprising electron transporting polymer, PGIA2 emitter and compound of the invention was deposited by spin-coating from a o-xylene solution in a glove box as shown below. Comparative devices wherein the compound of the invention is absent were also deposited by spin-coating from a o-xylene solution in a glove box. The precise conditions used for different light emitting layers are shown below.

| Polymer | Solvent | Conc w % |
|---|---|---|
| ETP:PGIA2 [60:40 w %] | ortho-xylene | 2.0 |
| ETP:PGIA2 [70:30 w %] | ortho-xylene | 2.0 |
| ETP:PGIA2 [90:10 w %] | ortho-xylene | 1.8 |
| ETP:PGIA2:Ie [55:10:35 w %] | ortho-xylene | 2.5 |
| ETP:PGIA2:Ie [50:10:40 w %] | ortho-xylene | 2.5 |
| ETP:PGIA2:Ie [45:10:45 w %] | ortho-xylene | 2.5 |
| ETP:PGIA2:Ie [40:10:50 w %] | ortho-xylene | 2.5 |
| ETP:PGIA2 [95:5 w %] | ortho-xylene | 2.0 |
| ETP:PGIA2:If [55:5:40 w %] | ortho-xylene | 2.0 |
| ETP:PGIA2:If [75:5:20 w %] | ortho-xylene | 2.0 |
| ETP:PGIA2:If [85:5:10 w %] | ortho-xylene | 2.0 |
| ETP:PGIA2 [70:30 w %] | ortho-xylene | 2.0 |
| ETP:PGIA2:Ig [55:5:40 w %] | ortho-xylene | 2.0 |
| ETP:PGIA2:Ig [75:5:20 w %] | ortho-xylene | 2.0 |
| ETP:PGIA2:Ig [85:5:10 w %] | ortho-xylene | 2.0 |

The light emitting layer was dried at 130° C. for 1e and at 100° C. for If and Ig for 10 minutes in a glove box. The light emitting layer has a thickness of 100 nm.

(v) Deposition of Cathode

The cathode was formed by formation of a layer of NaF by thermal evaporation to a thickness of 2 nm, followed by evaporation of a layer of Al to a thickness of 200 nm and a layer of silver to a thickness of 100 nm.

Testing of OLED Device

Current, voltage, and luminance drive characteristics are collected for device performance screening using characterised silicon photodiodes and device spectral output characteristics collected using a calibrated spectrometer system and collection optics. The device is typically swept through a voltage range, and IVL data curves are collected, the condition, timings and parameters under which measurements are made are controlled. Refined drive characteristics are collected using traceably calibrated, industry standard, photometry, colour measurement systems, power supplies and meters.

Life time is screened using photodiode based measuring systems, these monitor the device luminance and applied voltage, while it being driven by calibrated power supplies under specified conditions (constant current). The environmental conditions under which tests are carried out are stringently controlled.

Modelling of HOMO levels was carried out using AM1 semiempirical quantum chemical program implemented in the Hyperchem software.

Example 1

Figure 4A:
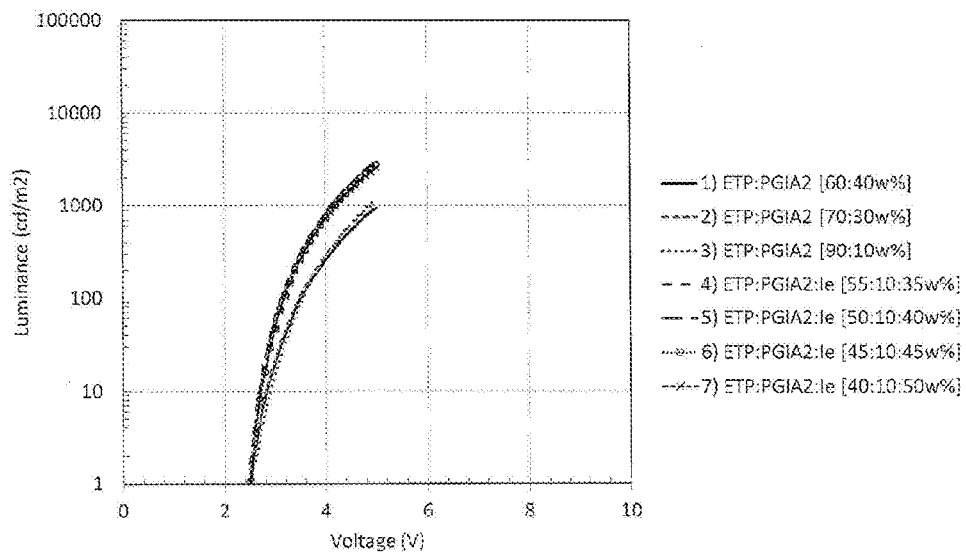
FIG. 4A shows a plot of luminance (cd/m$^2$) versus voltage (V) for devices having a light emitting layer comprising varying amounts of compound of the invention and comparative devices having a light emitting layer without compounds of the invention.
Figure 4B:
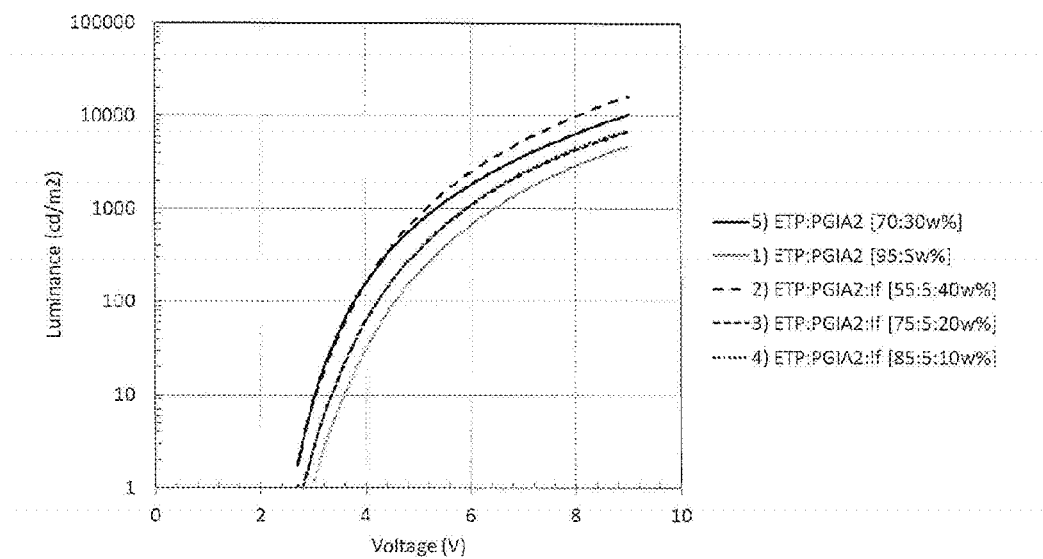
FIG. 4B shows a plot of luminance (cd/m$^2$) versus voltage (V) for devices having a light emitting layer comprising varying amounts of compound of the invention and comparative devices having a light emitting layer without compounds of the invention.
Figure 4C:
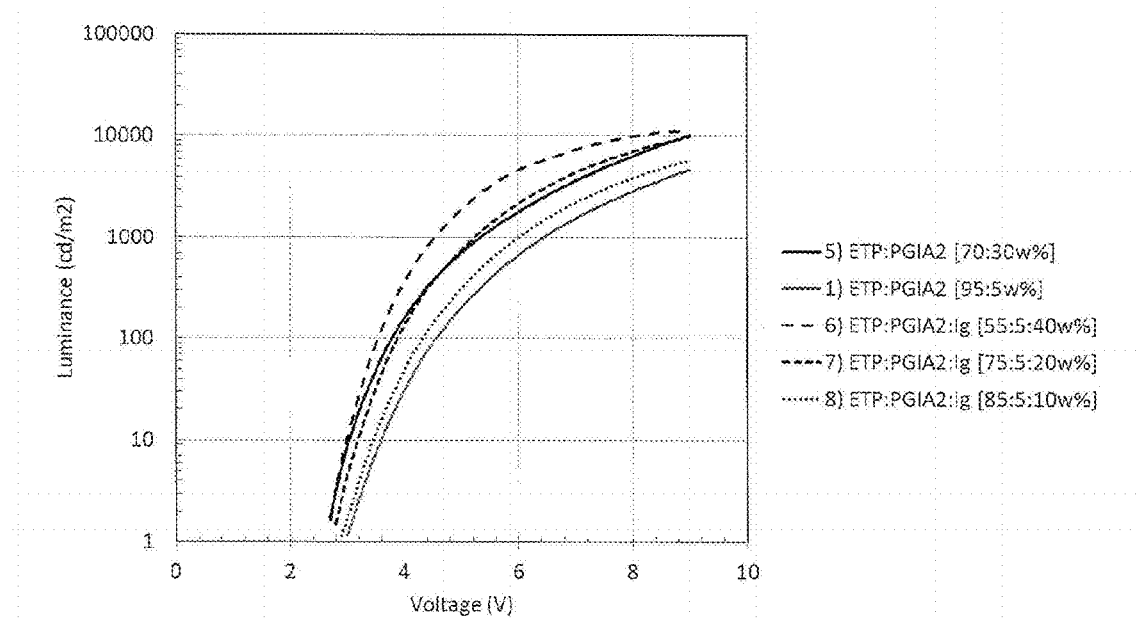
FIG. 4C shows a plot of luminance (cd/m$^2$) versus voltage (V) for devices having a light emitting layer comprising varying amounts of compound of the invention and comparative devices having a light emitting layer without compounds of the invention.

The luminance vs. voltage characteristic of OLEDs containing varying amounts of compound (Ie), (If) or (Ig) in each of their light emitting layers was measured. Control devices containing no compound of the invention were also fabricated and their luminance vs. voltage characteristic measured. The results are illustrated in FIGS. 4A-4C and Tables 1a and 1b.

TABLE 1a

| Light emitting layer composition | Median V @ 1000 cd/m$^2$ |
|---|---|
| 1) ETP:PGIA2 (60:40 wt %) | 5.0 |
| 2) ETP:PGIA2 (70:30 wt %) | 4.9 |
| 3) ETP:PGIA2 (90:10 wt %) | 4.8 |
| 4) ETP:PGIA2:Ie (55:10:35 wt %) | 4.1 |
| 5) ETP:PGIA2:Ie (50:10:40 wt %) | 4.1 |
| 6) ETP:PGIA2:Ie (45:10:45 wt %) | 4.2 |
| 7) ETP:PGIA2:Ie (40:10:50 wt %) | 4.2 |

It can be seen that adding the compound (Ie) to the light emitting layer lowers the drive voltage required in devices with low concentrations of PGIA2 emitter. For example, compositions 3 and 4 both contain 10 wt % PGIA2 emitter; composition 4, with 35 wt % compound (Ie), has a median drive voltage which is 0.7 V lower at 1000 cd/m$^2$ than composition 3, in which no such compound is present. Additionally composition 1 comprising 40 wt % PGIA2 and composition 4 comprising a total of 45 wt % of PGIA2 and compound (Ie) can be compared. Composition 4 has a drive voltage that is 0.9 V lower at 1000 cd/m$^2$. This corresponds to a significant improvement in device performance, in addition to offering a significant reduction in cost of compound (Ie) in comparison to PGIA2.

TABLE 1b

| Light emitting layer composition | Median V @ 1000 cd/m$^2$ |
|---|---|
| ETP:PGIA2: [70:30 w %] | 5.3 |
| ETP:PGIA2 [95:5 w %] | 6.4 |
| ETP:PGIA2:If [55:5:40 w %] | 5.2 |
| ETP:PGIA2:If [75:5:20 w %] | 5.9 |

TABLE 1b-continued

| Light emitting layer composition | Median V @ 1000 cd/m² |
|---|---|
| ETP:PGIA2:If [85:5:10 w %] | 5.9 |
| ETP:PGIA2:Ig [55:5:40 w %] | 4.5 |
| ETP:PGIA2:Ig [75:5:20 w %] | 5.2 |
| ETP:PGIA2:Ig [85:5:10 w %] | 6.0 |

Again it can be seen that adding the compound (If) or (Ig) to the light emitting layer lowers the drive voltage required in devices with low concentrations of PGIA2 emitter.

It can therefore be concluded that adding a compound of the invention results in lower drive voltages in devices that have a low concentration of iridium emitter in their light emitting layer.

Example 2

Figure 5A:
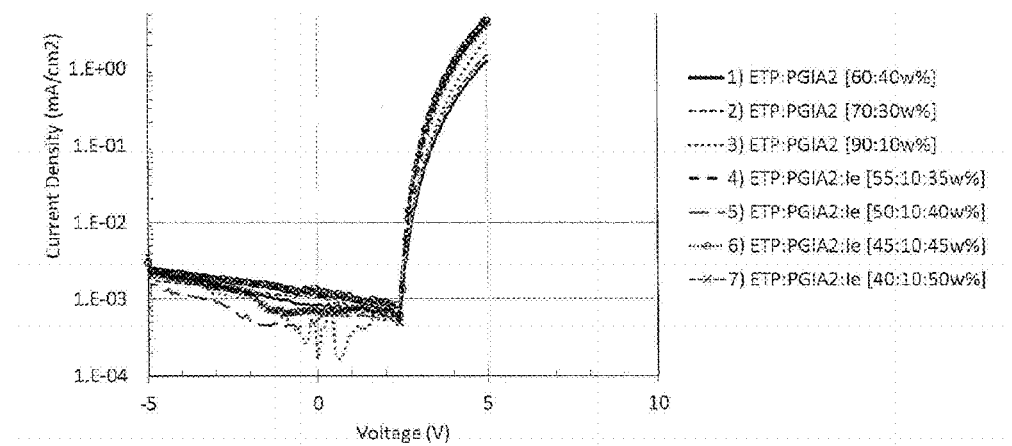
FIG. 5A shows a plot of current density (mA/cm$^2$) versus voltage (V) for devices having a light emitting layer comprising varying amounts of compound of the invention and comparative devices having a light emitting layer without compounds of the invention.
Figure 5B:
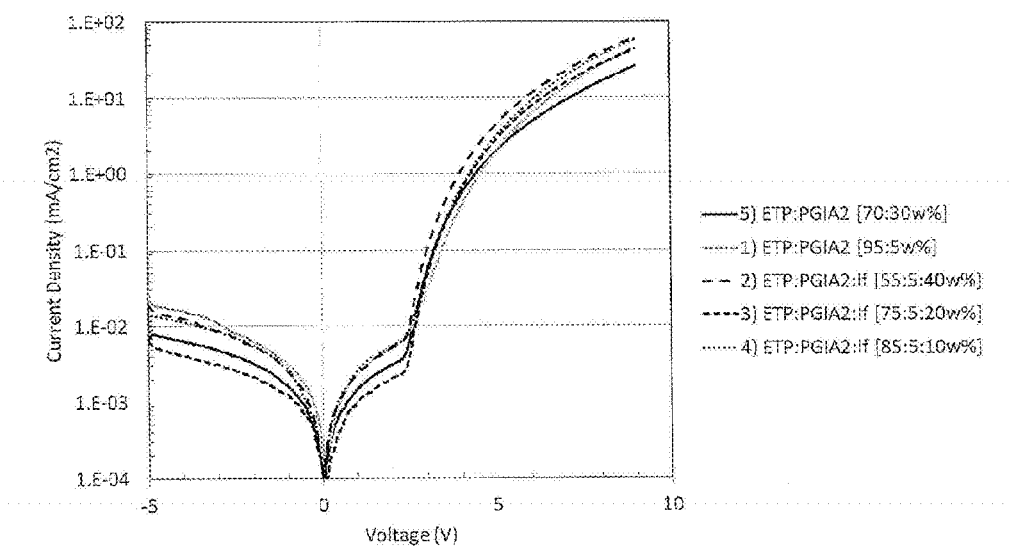
FIG. 5B shows a plot of current density (mA/cm$^2$) versus voltage (V) for devices having a light emitting layer comprising varying amounts of compound of the invention and comparative devices having a light emitting layer without compounds of the invention.
Figure 5C:
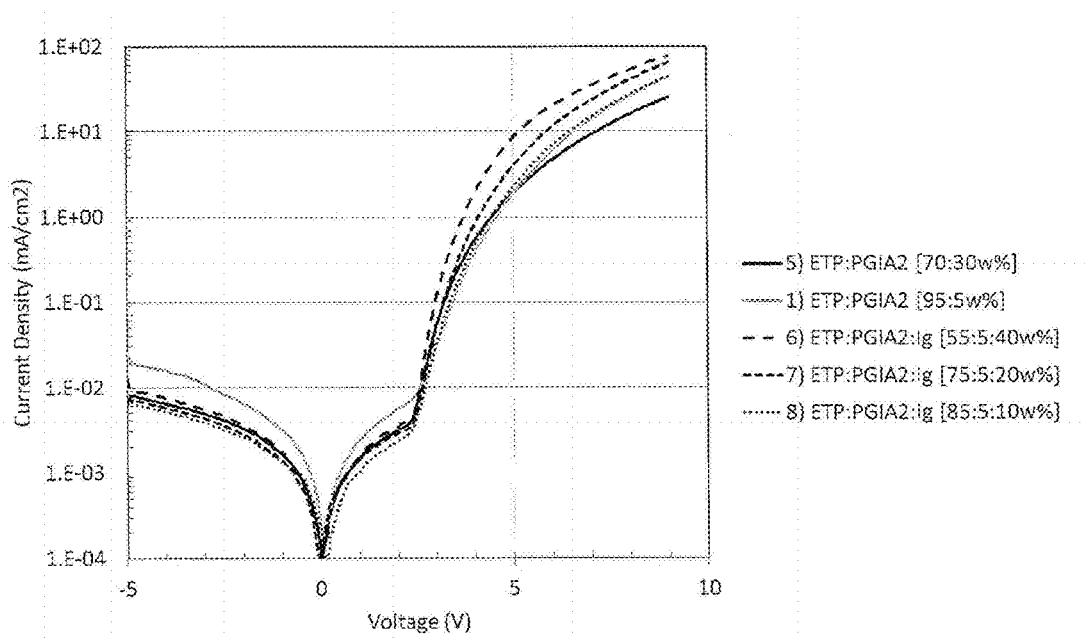
FIG. 5C shows a plot of current density (mA/cm$^2$) versus voltage (V) for devices having a light emitting layer comprising varying amounts of compound of the invention and comparative devices having a light emitting layer without compounds of the invention.

The current density vs. voltage profiles of devices containing varying amounts of compound of the invention and control devices, with no such compound, were measured. The results are shown in FIGS. 5A-C and Tables 2a and 2b.

TABLE 2a

| Light emitting layer composition | Median J @ 4 V |
|---|---|
| 1) ETP:PGIA2 (60:40 wt %) | 1.3 |
| 2) ETP:PGIA2 (70:30 wt %) | 1.5 |
| 3) ETP:PGIA2 (90:10 wt %) | 2.4 |
| 4) ETP:PGIA2:Ie (55:10:35 wt %) | 5.0 |
| 5) ETP:PGIA2:Ie (50:10:40 wt %) | 4.5 |
| 6) ETP:PGIA2:Ie (45:10:45 wt %) | 4.2 |
| 7) ETP:PGIA2:Ie (40:10:50 wt %) | 4.1 |

It can be seen that reducing the concentration of PGIA2 in the host polymer results in a small increase in current density. Adding 35-50 wt % compound (Ie) results in a substantial increase in current density, suggesting that compound (Ie) improves hole supply when low quantities of PGIA2 emitter are present.

TABLE 2b

| Light emitting layer composition | V@10 mA/cm² |
|---|---|
| 5) ETP:PGIA2: [70:30 w %] | 7.0 |
| 1) ETP:PGIA2 [95:5 w %] | 6.6 |
| 2) ETP:PGIA2:If [55:5:40 w %] | 5.7 |
| 3) ETP:PGIA2:If [75:5:20 w %] | 6.3 |
| 4) ETP:PGIA2:If [85:5:10 w %] | 6.1 |
| 6) ETP:PGIA2:Ig [55:5:40 w %] | 5.1 |
| 7) ETP:PGIA2:Ig [75:5:20 w %] | 5.9 |
| 8) ETP:PGIA2:Ig [85:5:10 w %] | 6.4 |

Again it can be seen that increasing the concentration of compound of the invention results in an increase in current density.

It can therefore be concluded that adding a compound of the invention improves hole supply and results in higher current densities in devices with a low concentration of iridium emitter.

Example 3

Figure 6A:
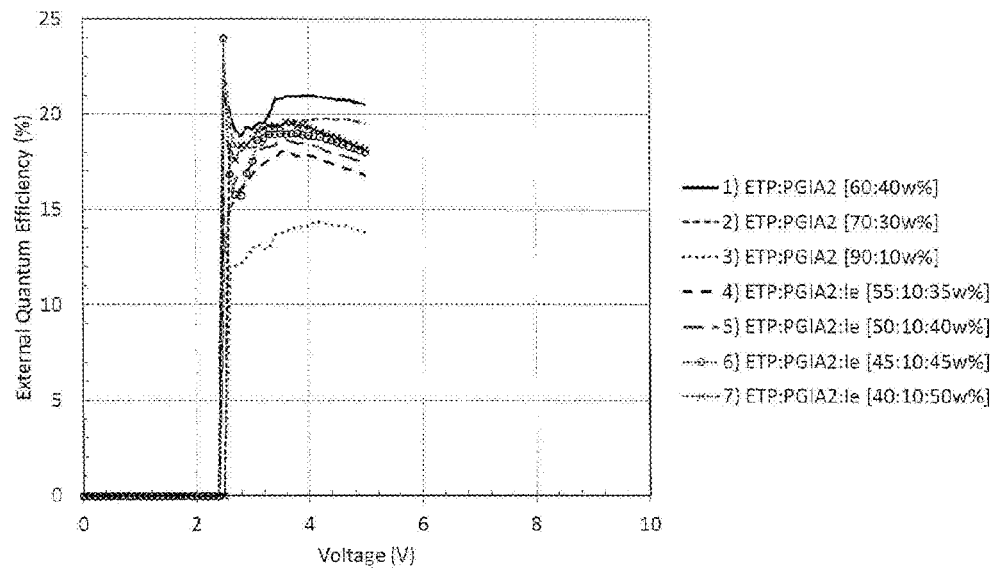
FIG. 6A shows a plot of EQE versus voltage for devices having a light emitting layer comprising varying amounts of compound of the invention and comparative devices having a light emitting layer without compounds of the invention.
Figure 6B:
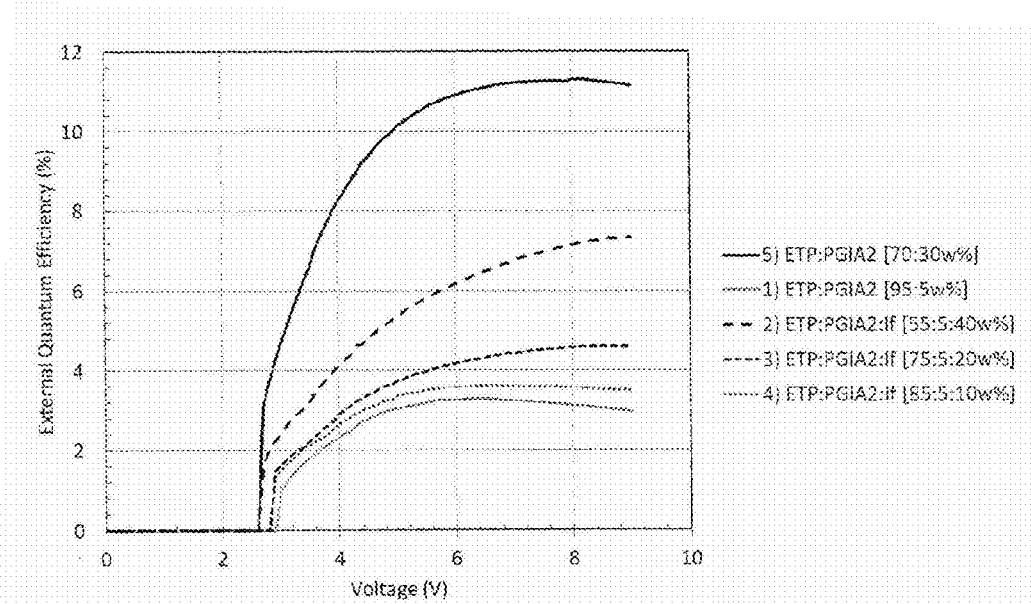
FIG. 6B shows a plot of EQE versus voltage for devices having a light emitting layer comprising varying amounts of compound of the invention and comparative devices having a light emitting layer without compounds of the invention.
Figure 6C:
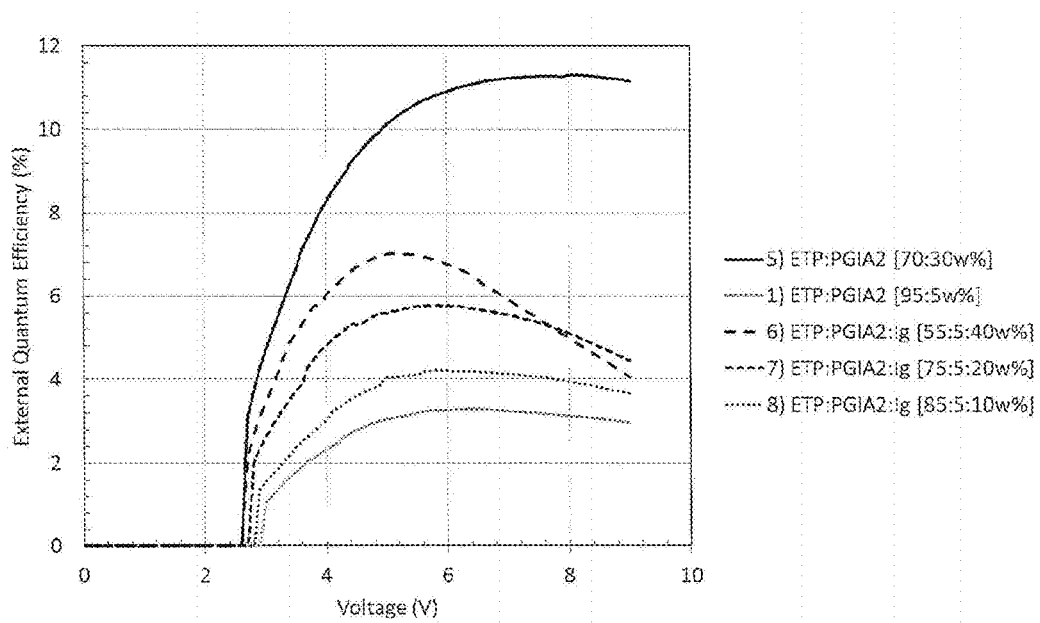
FIG. 6C shows a plot of EQE versus voltage for devices having a light emitting layer comprising varying amounts of compound of the invention and comparative devices having a light emitting layer without compounds of the invention.

The external quantum efficiency (EQE) vs. voltage plots of devices containing varying amounts of compound of the invention, and control devices with no compound but varying amounts of PGIA2 emitter, were measured. The results are shown in FIGS. 6A-6C and Tables 3a and 3b.

TABLE 3a

| Light emitting layer composition | Median EQE @ 1000 cd/m² |
|---|---|
| 1) ETP:PGIA2 (60:40 wt %) | 21.0 |
| 2) ETP:PGIA2 (70:30 wt %) | 19.6 |
| 3) ETP:PGIA2 (90:10 wt %) | 14.0 |
| 4) ETP:PGIA2:Ie (55:10:35 wt %) | 17.7 |
| 5) ETP:PGIA2:Ie (50:10:40 wt %) | 18.3 |
| 6) ETP:PGIA2:Ie (45:10:45 wt %) | 18.8 |
| 7) ETP:PGIA2:Ie (40:10:50 wt %) | 19.1 |

It can be seen from compositions 1, 2 and 3 that reducing the concentration of PGIA2 from 40 to 10 wt % results in a sharp drop of EQE from 21.0 to 14.0% @ 1000 cd/m². Compositions 4-7 all contain only 10 wt % PGIA2, but from 35-50 wt % of compound (Ie). There is a clear upwards trend in EQE as the concentration of compound (Ie) is increased, with compositions 6 and 7 having comparable EQE to devices containing three times as much PGIA2 emitter (composition 2). Composition 7, with 50 wt % compound (Ie) and 10 wt % PGIA2, has 98% of the EQE of composition 2, which contains 30 wt % PGIA2. Thus it is demonstrated that the addition of compound (Ie) increases the EQE of devices containing low concentrations of PGIA2 emitter in the light emitting layer.

A similar upwards trend in EQE is also observed with increasing concentration of compound (If) and (Ig).

TABLE 3b

| Light emitting layer composition | Median EQE @ 1000 cd/m² |
|---|---|
| 5) ETP:PGIA2: [70:30 w %] | 11.4 |
| 1) ETP:PGIA2 [95:5 w %] | 3.3 |
| 2) ETP:PGIA2:If [55:5:40 w %] | 7.3 |
| 3) ETP:PGIA2:If [75:5:20 w %] | 4.6 |
| 4) ETP:PGIA2:If [85:5:10 w %] | 3.6 |
| 6) ETP:PGIA2:Ig [55:5:40 w %] | 7.0 |
| 7) ETP:PGIA2:Ig [75:5:20 w %] | 5.8 |
| 8) ETP:PGIA2:Ig [85:5:10 w %] | 4.2 |

It can therefore be concluded that adding a compound of the invention improves hole supply and enables high EQEs to be achieved in combination with low concentrations of the iridium PGIA2 emitter.

Example 4

The stability of devices was tested by measuring their luminance as a function of time. The device of the invention and the comparative devices were fabricated by the same process but having light emitting layers as described below:

Device of invention comprised electron transporting polymer, PGIA2 and compound (Ie) (56.5:4.4:39.1 wt % ratio)

Comparative device A solely comprised electron transporting polymer and PGIA2 in its light emitting layer (95:5 wt % ratio)

Comparative device B comprised electron transporting polymer, PGIA2 and a dendrimer (50.2:3.9:45.9 wt % ratio) as shown below which is representative of dendrimers disclosed in the prior art.

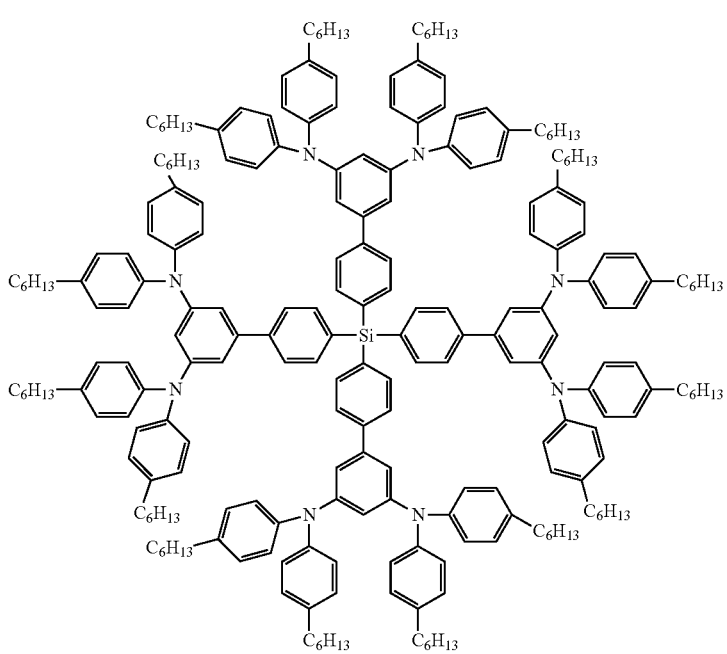

P

Figure 7:
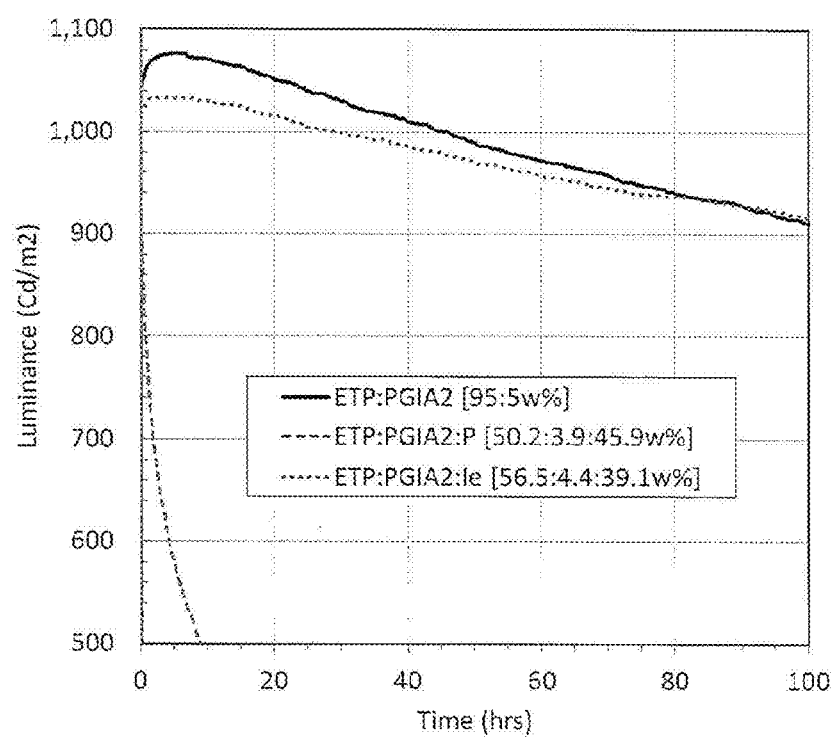
FIG. 7 shows a plot of luminance (cd/m$^2$) versus time (hours) for a device having a light emitting layer comprising a compound of the invention and two comparative devices, one having a light emitting layer comprising a known dendrimer and one having a light emitting layer comprising only conventional iridium emitter.

The results can be seen in FIG. 7. It can be seen that the device containing the dendrimer P shown above has a markedly decreased lifetime, with the luminance dropping sharply and reaching 0 after around 10 hours. In contrast, the device containing the compound of the invention has a comparable luminance vs. time plot as the device which contains no such compound, illustrating that the presence of the compound of the invention does not significantly contribute to device degradation over time in devices with low concentrations of PGIA2 emitter.

Example 5

Figure 8A:
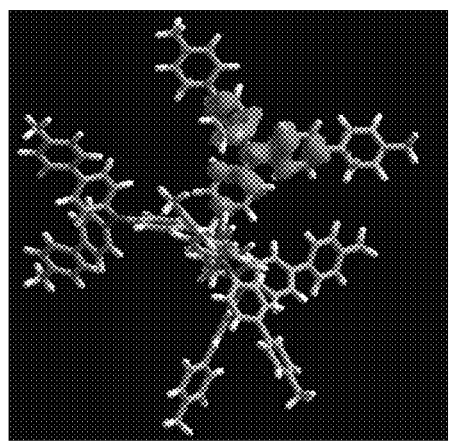
FIG. 8A shows the spacial characteristics of HOMO levels (as determined by AM1 QC modelling) in a compound of the invention.
Figure 8B:
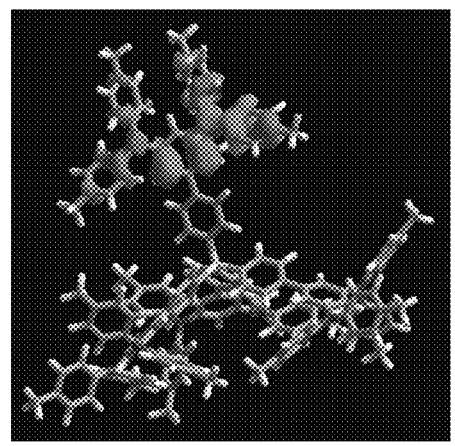
FIG. 8B shows the spacial characteristics of HOMO levels (as determined by AM1 QC modelling) in a comparative compound.

The geometries of compound (Ie) and of the dendrimer P were calculated using the semiempirical AM1 method, followed by modelling of the spatial characteristics of the HOMO levels. The results highlighted a significant difference (see FIG. 8). FIG. 8A shows the spatial arrangement of the HOMO level of compound (Ie), and shows that the HOMO is predominantly localised in the core of the dendrons, where it is relatively inaccessible. In contrast, the spatial characteristics of the HOMO level of dendrimer P is such that the HOMO extends to the terminal phenyl units of the dendrons, and hence the "surface" of the dendrimer. Without wishing to be bound by theory it is hypothesised that this difference in HOMO spatial arrangement is at least partly why device degradation with compound Ie occurs at a much slower rate than with dendrimer P. We suggest the following explanation:

During hole transport by Ie or dendrimer P, the localisation of the positive charge is similar to the spatial characteristics of the respective HOMO level. In the case of compound Ie, the positive charge will therefore be predominantly localised in the core of the dendrons, and therefore be sterically shielded from interaction with negatively charged locations on the electron transporting host polymer during device operation. In contrast, the positive charge on dendrimer P has a non-negligible probability of residing on the "surface" of the dendrimer, and can therefore easily interact with negative charges on the electron transporting host polymer. Thus without wishing to be bound by theory, we hypothesise that interactions between positive charges on hole transporting materials and negative charges on the host polymer during device operation may result in changes that contribute to device degradation.

The invention claimed is:

1. An organic optoelectronic device comprising an anode, a cathode and an active organic layer in between said anode and cathode, wherein said active organic layer comprises a compound of general formula (I):

(I)

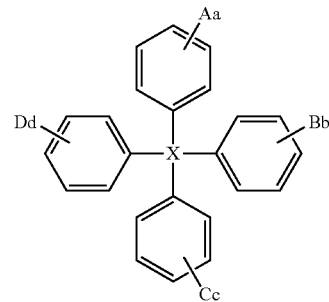

wherein
X is C, Si or Ge;
A is a group of formula (II)

(II)

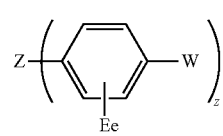

wherein Z is N, P, NH, O or S;
E is $C_{1-10}$ alkyl or H;
W is substituted or unsubstituted $C_{5-14}$ aryl;
e is an integer from 1 to 4; and
z is 1 or 2;
B, C and D are each independently A, H, $C_1$-$C_{12}$ alkyl, $C_{5-14}$ aryl or OH; and
a, b, c and d are each independently an integer from 1 to 5 wherein W is an aryl group selected from phenyl, naphthyl, indanyl, indenyl, tetrahydronaphthalenyl, pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, quinoxalinyl, phthalamidyl, phthalic anhydride, indolinyl, isoindolinyl, tetrahydroisoquinolinyl, fluorenyl and carbazolyl.

2. The device as claimed in claim 1, wherein X is Si.

3. The device as claimed in claim 1, wherein a is 1 or 2.

4. The device as claimed in claim 1, wherein the compound of general formula (I) has formula (Ia):

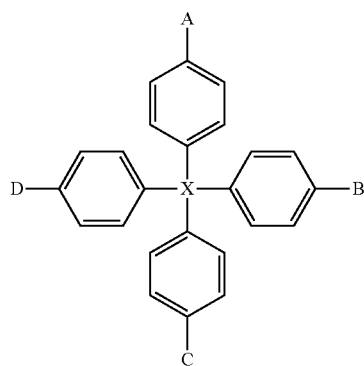

(Ia)

wherein X, A, B, C and D are as defined in claim 1.

5. The device as claimed in claim 4, wherein each of A, B, C and D are the same group of formula (II).

6. The device as claimed in claim 1, wherein the compound of general formula (I) has formula (Ib):

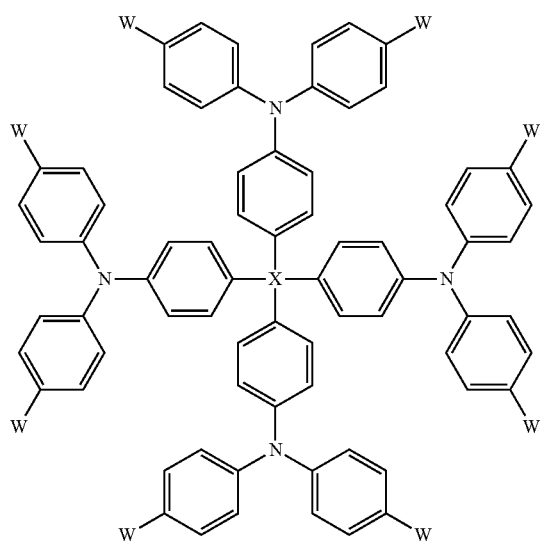

(Ib)

wherein X and W are as defined in claim 1.

7. The device as claimed in claim 6, wherein W is a phenyl group.

8. The device as claimed in claim 6, wherein W is a substituted aryl group.

9. The device as claimed in claim 1, wherein the compound of general formula (I) has formula (Ic):

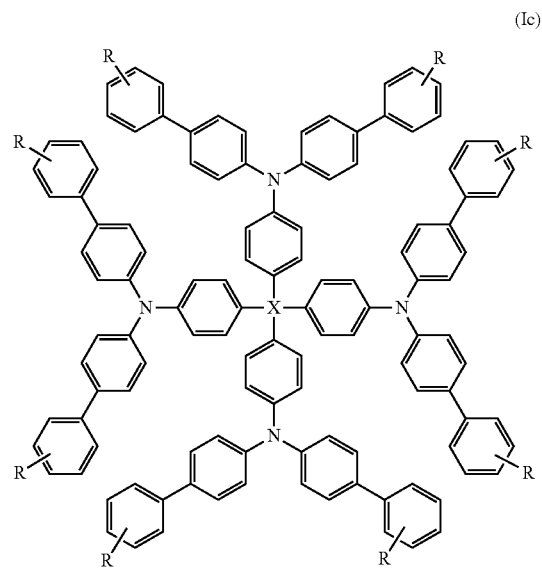

(Ic)

wherein X is as defined in claim 1 and R is selected from halogen, $C_{1-16}$ halocarbon, $C_{1-16}$ alkyl, $C_{2-16}$ alkenyl, $C_{2-16}$ alkynyl, $C_{1-16}$ alkoxy, $C_{5-14}$ aryl, heteroaryl and arylalkyl.

10. The device as claimed in claim 1, wherein the compound of general formula (I) has formula (Id):

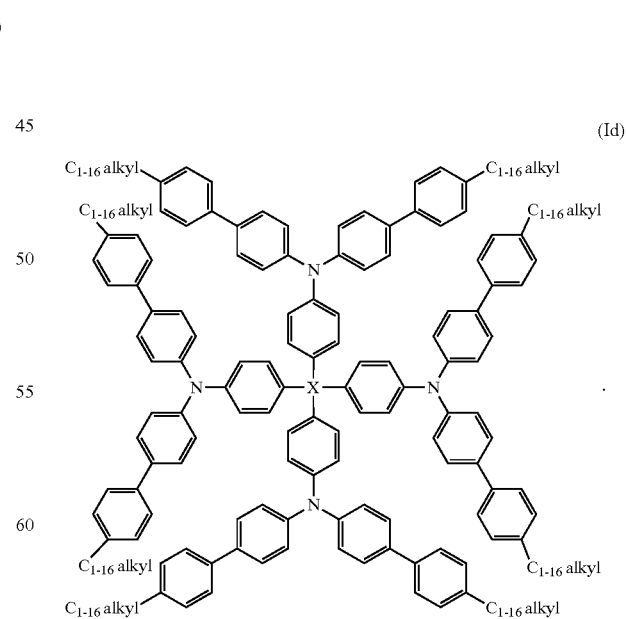

(Id)

11. The device as claimed in claim 1, wherein the compound of general formula (I) has formula (Ie):

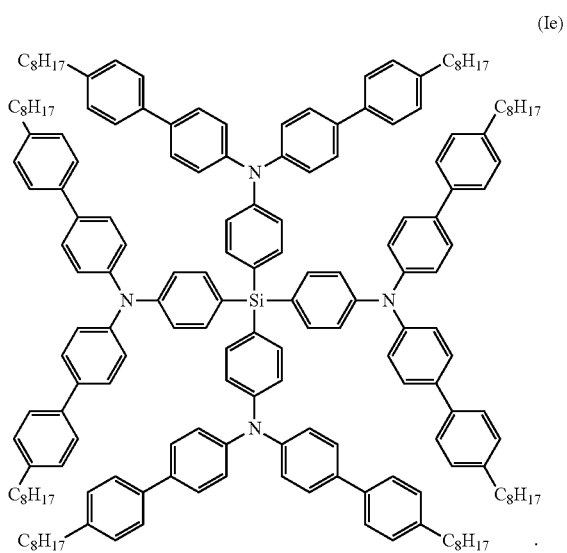

(Ie)

12. The device as claimed in claim 1, wherein the active organic layer comprises a blend of a compound of formula (I) and at least one of: (a) an electron transporting material or (b) a light emitting compound.

13. The device as claimed in claim 12, wherein the active organic layer comprises an electron transporting material, wherein said electron transporting material is a polymer.

14. The device as claimed in claim 12, wherein the active organic layer further comprises a light emitting compound, wherein said light emitting compound is a compound of formula (III):

$$ML^1_q L^2_r L^3_s \qquad (III)$$

wherein
M is a metal;
each of $L^1$, $L^2$ and $L^3$ is a ligand;
q is an integer;
r and s are each independently 0 or an integer; and
the sum of (a. q)+(b. r)+(c.s) is equal to the number of coordination sites available on M, wherein a is the number of ligating sites on $L^1$, b is the number of ligating sites on $L^2$ and c is the number of ligating sites on $L^3$.

15. The device as claimed in claim 12, wherein the blend comprises 20-50 wt. % compound of formula (I); 7.5-12.5 wt. % light emitting compound; and 40-60 wt. % electron transporting polymer.

16. The device as claimed in claim 1, wherein the device is an organic light emitting device and the active organic layer is an organic light-emitting layer.

17. The device as claimed in claim 1, wherein the device comprising:
(i) a substrate;
(ii) an anode on said substrate;
(iii) a hole injection layer on said anode;
(iv) a light emitting layer on said hole injection layer; and
(v) a cathode on said light emitting layer,
wherein said light emitting layer comprises said active organic layer comprising a compound of general formula (I).

18. The device as claimed in claim 1, wherein E is H.

19. The device as claimed in claim 1, wherein Z is N or P and z is 2.

* * * * *